(12) United States Patent
Bandoh et al.

(10) Patent No.: US 9,061,090 B2
(45) Date of Patent: Jun. 23, 2015

(54) STEM STRUCTURE FOR COMPOSITE PROSTHETIC HIP AND METHOD FOR MANUFACTURING THE SAME

(75) Inventors: Shunichi Bandoh, Kakamigahara (JP); Kojima Kisanuki, Kakamigahara (JP); Shigeru Hibino, Kakamigahara (JP)

(73) Assignee: KABUSHIKI KAISHA B.I. TEC, Gifu (JP)

( * ) Notice: Subject to any disclaimer, the term of this patent is extended or adjusted under 35 U.S.C. 154(b) by 507 days.

(21) Appl. No.: 13/635,546

(22) PCT Filed: Mar. 17, 2011

(86) PCT No.: PCT/JP2011/056476
§ 371 (c)(1),
(2), (4) Date: Oct. 15, 2012

(87) PCT Pub. No.: WO2011/115229
PCT Pub. Date: Sep. 22, 2011

(65) Prior Publication Data
US 2013/0030546 A1    Jan. 31, 2013

(30) Foreign Application Priority Data
Mar. 17, 2010   (JP) .................. 2010-061067

(51) Int. Cl.
*A61F 2/36*    (2006.01)
*A61L 27/44*   (2006.01)
*A61F 2/30*    (2006.01)

(52) U.S. Cl.
CPC ............... *A61L 27/443* (2013.01); *A61F 2/36* (2013.01); *A61F 2002/30957* (2013.01);
(Continued)

(58) Field of Classification Search
CPC ............. A61F 2/36–2/3676; A61F 2/3859; A61F 2/3868; A61F 2/389; A61F 2/4059; A61L 27/443; A61L 27/40; A61L 27/42; A61L 27/422
USPC .................. 623/23.51, 23.58–23.61
See application file for complete search history.

(56) References Cited

U.S. PATENT DOCUMENTS 3,556,922 A * 1/1971 Green et al. .................... 428/98
3,707,006 A * 12/1972 Bokros et al. ................. 424/422
(Continued)

FOREIGN PATENT DOCUMENTS

JP          2001347572 A    12/2001

OTHER PUBLICATIONS

International Search Report, for PCT/JP2011/056476, mailed Apr. 19, 2011, 2 pages.

*Primary Examiner* — Alvin Stewart
(74) *Attorney, Agent, or Firm* — Ware, Fressola, Maguire & Barber, LLP

(57) ABSTRACT

A stem 8 has the following elements made from FRP: an upper outer shell 4U, a main structure upper half 3U, a main structure lower half 3L, and a lower outer shell 4L when the stem is placed in a flat state. The elements are integrated into one piece by stacking the elements and applying heat and pressure to melt resins impregnated in the FRP structural elements. Each outer shell is a curved prepreg sheet formed by impregnating carbon fibers arranged at angle of ±45 degrees with a thermoplastic resin, and each upper and lower halve is an evenly stacked part in which prepreg sheets are stacked. Overlapping section 5 of the upper and lower outer shells are formed such that the left and right portions of a main structure 3 formed by integrating the upper and lower halves 3U, 3L does not have a stepped outer surface.

6 Claims, 26 Drawing Sheets

(52) U.S. Cl.
CPC ......... *A61L 2430/02* (2013.01); *A61F 2/30965* (2013.01); *A61F 2002/30971* (2013.01); *A61F 2002/30975* (2013.01)

(56) References Cited

U.S. PATENT DOCUMENTS

| | | | |
|---|---|---|---|
| 3,893,196 A * | 7/1975 | Hochman | 424/422 |
| 3,901,717 A * | 8/1975 | Revaz | 428/539.5 |
| 4,157,181 A * | 6/1979 | Cecka | 473/319 |
| 4,221,623 A * | 9/1980 | Heissler et al. | 156/169 |
| 4,268,468 A * | 5/1981 | Esper et al. | 264/131 |
| 4,329,743 A * | 5/1982 | Alexander et al. | 623/13.18 |
| 4,356,571 A * | 11/1982 | Esper et al. | 424/423 |
| 4,411,027 A * | 10/1983 | Alexander et al. | 623/13.18 |
| 4,512,038 A * | 4/1985 | Alexander et al. | 623/23.75 |
| 4,657,717 A * | 4/1987 | Cattanach et al. | 264/102 |
| 4,683,018 A * | 7/1987 | Sutcliffe et al. | 156/196 |
| 4,750,905 A * | 6/1988 | Koeneman et al. | 623/23.51 |
| 4,892,552 A * | 1/1990 | Ainsworth et al. | 623/23.34 |
| 4,902,297 A * | 2/1990 | Devanathan | 623/23.51 |
| 4,978,360 A * | 12/1990 | Devanathan | 264/136 |
| 4,997,444 A * | 3/1991 | Farling | 623/23.51 |
| 5,064,439 A * | 11/1991 | Chang et al. | 264/255 |
| 5,163,962 A * | 11/1992 | Salzstein et al. | 623/23.34 |
| 5,181,930 A * | 1/1993 | Dumbleton et al. | 623/23.34 |
| 5,192,330 A * | 3/1993 | Chang et al. | 623/23.34 |
| 5,314,492 A * | 5/1994 | Hamilton et al. | 623/23.34 |
| 5,326,354 A * | 7/1994 | Kwarteng | 427/2.24 |
| 5,397,358 A * | 3/1995 | Wenner et al. | 623/23.51 |
| 5,397,365 A * | 3/1995 | Trentacosta | 623/18.11 |
| 5,443,513 A * | 8/1995 | Moumene et al. | 623/23.51 |
| 5,518,399 A * | 5/1996 | Sicurelli et al. | 433/220 |
| 5,522,904 A * | 6/1996 | Moran et al. | 623/23.34 |
| 5,591,233 A * | 1/1997 | Kelman et al. | 623/23.51 |
| 5,593,451 A * | 1/1997 | Averill et al. | 623/23.15 |
| 5,593,452 A * | 1/1997 | Higham et al. | 623/23.38 |
| 5,609,638 A * | 3/1997 | Price et al. | 623/20.32 |
| 5,609,646 A * | 3/1997 | Field et al. | 623/22.32 |
| 5,915,970 A * | 6/1999 | Sicurelli et al. | 433/220 |
| 5,919,044 A * | 7/1999 | Sicurelli et al. | 433/220 |
| 5,981,827 A * | 11/1999 | Devlin et al. | 623/23.51 |
| 6,132,470 A * | 10/2000 | Berman | 623/23.15 |
| 6,228,123 B1 * | 5/2001 | Dezzani | 623/23.32 |
| 6,287,122 B1 * | 9/2001 | Seeram et al. | 433/220 |
| 6,299,649 B1 * | 10/2001 | Chang et al. | 623/23.34 |
| 6,371,763 B1 * | 4/2002 | Sicurelli et al. | 433/220 |
| 6,500,206 B1 * | 12/2002 | Bryan | 623/17.16 |
| 6,641,893 B1 * | 11/2003 | Suresh et al. | 428/105 |
| 6,676,704 B1 * | 1/2004 | Pope et al. | 623/18.11 |
| 6,709,463 B1 * | 3/2004 | Pope et al. | 623/23.51 |
| 6,905,517 B2 * | 6/2005 | Bonutti | 623/23.63 |
| 7,673,550 B2 * | 3/2010 | Karmaker et al. | 87/1 |
| 7,947,135 B2 * | 5/2011 | Fonte | 148/563 |
| 7,997,901 B2 * | 8/2011 | Karmaker | 433/224 |
| 8,062,378 B2 * | 11/2011 | Fonte | 623/23.26 |
| 8,137,486 B2 * | 3/2012 | Fonte | 148/563 |
| 8,333,803 B2 * | 12/2012 | Park et al. | 623/13.14 |
| 8,398,790 B2 * | 3/2013 | Fonte | 148/563 |
| 8,603,181 B2 * | 12/2013 | Pope et al. | 623/22.21 |
| 8,790,402 B2 * | 7/2014 | Monaghan et al. | 623/16.11 |
| 2006/0184250 A1 * | 8/2006 | Bandoh et al. | 623/23.32 |
| 2008/0195218 A1 * | 8/2008 | Jones | 623/20.36 |
| 2008/0234833 A1 * | 9/2008 | Bandoh et al. | 623/23.15 |
| 2008/0262629 A1 * | 10/2008 | Fonte | 623/23.15 |
| 2009/0204226 A1 * | 8/2009 | Fonte | 623/23.15 |
| 2010/0210745 A1 * | 8/2010 | McDaniel et al. | 521/55 |
| 2010/0312354 A1 * | 12/2010 | Bandoh et al. | 623/23.15 |
| 2012/0123553 A1 * | 5/2012 | Sidebotham et al. | 623/23.15 |
| 2013/0030546 A1 * | 1/2013 | Bandoh et al. | 623/23.34 |
| 2014/0287641 A1 * | 9/2014 | Steiner, III | 442/223 |

* cited by examiner

STEM STRUCTURE FOR COMPOSITE PROSTHETIC HIP AND METHOD FOR MANUFACTURING THE SAME

TECHNICAL FIELD

The present invention relates to a stem structure for composite prosthetic hip and a method for manufacturing the same, more particularly, to a femur prosthesis formed by stacking FRP (fiberglass reinforced plastics) materials which are much more appropriate than metal materials for a stem to be custom-made, and a method for manufacturing the same.

BACKGROUND ART

A composite material formed by impregnating carbon fiber with resin as matrix is lighter and higher both in longitudinal elastic modulus and in fatigue strength than those of a metallic material, therefore, it is quite possible that the composite material is appropriate to a prosthesis for hip joint broken due to a traffic accident or the like. However, the composite material has unavoidable anisotropy caused by woven cloth used as reinforcement, thus making it difficult to have the same isotropy as a metallic stem has. Yet, there is a possibility of obtaining pseudo-isotropy by alternately changing the direction of fiber of woven cloth, so that the method has been very well researched of introducing the composite material into artificial hip prosthesis stem.

A hip joint consists of a caput as a spherical joint which enables a personal body to rotate and bend by engaging with an acetabulum of pelvis and a neck connecting the caput with a femur. If the spherical joint is damaged, the hip joint loses its proper function. In order to recover it, the acetabulum is in need of repair, or as shown in FIG. 25 the pelvis and the neck are in need of replacement with a ball 31 and a stem 8 supporting the ball on the femur respectively as substitutes. The stem comprises a neck 1 supporting the ball in position and a body 2 fixing the neck to the femur.

The stem 8, when made of FRP, has a composite structure of, for example, woven cloth of carbon and a resin impregnated in the woven cloth, such as PEEK which is harmless to the human. The stem is formed by stacking the FRP materials in the cross section thereof with the materials concavely curved so as to fit the outer shape of the stem. More particularly, the stem is divided in the anterior and posterior direction of human body into two halves which mate together to form the stem. The divided surface 32 is selected so as to contain a longitudinal reference line 8a linking a center 1a on the end of the neck and a center 2a in the diaphysis of the distal portion of the stem. Each of the two halves is placed in a flat state to have an upper half 8U and a lower half 8L respectively. The FRP sheets are stacked in each of the molds where these upper and lower halves are formed. The upper half corresponds to the anterior portion of the stem and the lower half corresponds to the posterior portion of the stem (in the figure the stem is for a left leg). The stem 8 in the center of the figure is illustrated by using a set of lines of the edge of the prepreg sheets on the widest cross section thereof.

The prepreg sheets, i.e., thin sheets formed by impregnating woven cloth such as carbon with a thermoplastic resin, are heated to be deformable, for being overlaid in contact with the contour 33 of the cavity of the mold D, as shown in FIG. 26(a). In principle, the whole of the sheet $7_i$ is covered with the sheet $7_{i+1}$ to be successively overlaid, thus multi-layers like growth rings of a tree may be formed in the mold. Applying the curing to the multi-layers in an autoclave enables the lower half 8L of the stem to obtain an outer shape that is identical to the cavity of the mold. The upper half of the stem which is formed in the same way as above, not shown, is stacked on the lower half, the two halves are contained in the mold to have the curing again, an FRP stem can be obtained whose neck 1 and body 2 are integrated. In U.S. Pat. No. 3,901,717 a method is disclosed that FRP is used for forming a stem.

With the stem 8 formed by curvedly stacking sheets like growth rings of a tree, air voids 34 are frequently produced on the cross section of the stem 8, as shown in FIG. 26(b). While the sheets are stacked, spaces 35 often remain between the sheets as shown in (c), which is an enlargement of section H of (a), but all the air cannot be squeezed out during the curing operation. On the Pascal's principle the pressure everywhere in the mold is uniformly maintained by the force F throughout the curing operation, and consequently it is impossible for the stem to have low-pressure area which enables release of the air, i.e., the sheets stick to each other at the both ends of the space where the air remains to form a closed area 35. The quality of stem depends mainly on an allowance for the quantity and the size of the air voids for producing the stem. Besides, in order to obtain pseudo-isotropy by stacking anisotropy sheets, it is necessary to alternately stack the sheets $7_i$ having fibers arranged at angle of 0/90 degrees and the sheets $7_{i+j}$ having fibers arranged at angle of ±45 degrees, however, which varies the direction of the plane rigidity every sheet, resulting in a decline in adherence of the sheets curvedly stacked.

In the field of optical molding, as disclosed in JP2001-347572A1, e.g., an desired shape of an object is obtained in the following method; contour lines of an object are calculated by level-cutting the three-dimensional data of the object, uncured photo-setting resin is sliced into some layers in uniform thickness on the basis of the contour lines, successively the layers are stacked to be integrated into one piece by curing.

When a three dimensional object is obtained by the optical molding, the primary purpose is to reproduce the outer shape of the object, not to obtain the structure so as to withstand complex loads, although it may be possible depending on the mechanical characteristics of cured resin. Even though a stem might be formed by using the method of optical molding, there is few possibility of obtaining a stem such that it can withstand tension, bending moment and shearing load caused by the influence of his weight or the like and has resistance to the load such as a hoop stress, what is more, these loads mentioned above will act irregularly. From this point of view, it is obvious that the FRP stacked product formed by applying the principle of optical molding thereto will not have the mechanical structure to be required as a stem.

DOCUMENTS OF PRIOR ART

[Patent Document 1] U.S. Pat. No. 3,901,717
[Patent Document 2] JP2001347572A1

DISCLOSURE OF INVENTION

Problems to be Solved

As mentioned above, an artificial hip prosthesis composite material stem ought to be pseudo-isotropic in spite of the fact that originally anisotropic materials are applied thereto and be a molded product having few air voids by closely stacking FRP materials as well. In order to obtain such a stem, much more advanced technology has to be applied to the current technology, on structure of the FRP elements to be determined for the stem, on designing the structure to withstand such peculiar load acting on the stem, on devices for the molds to form the structural elements, and on careful handling required during the curing operation. Thus, it will be possible in the near future to provide a low cost stem which fits patients perfectly in shape, whereas as to casting metal stems, patients have to select an acceptable one among ready-made metal stems of some typical shapes.

The object of the present invention is to solve the problems mentioned above in custom-making a stem which varies in shape from patient to patient; the first is to propose a stem which enables to prevent air voids from occurring by applying the technology of evenly stacking prepreg sheets to the process for forming the stem. The second object is to propose a structure of an artificial hip prosthesis composite material stem and a method of manufacturing thereof by means of evenly stacking sheets, which enables the stem to have desired strength, proof stress, and rigidity and to obtain a shape with high accuracy through the solution of mechanical and structural defects of the stem caused by curvedly stacking sheets.

Disclosure of Invention

The present invention is applied to an artificial hip prosthesis stem formed by stacking FRP (fiberglass reinforced plastics). Referring to FIG. 1, when a stem 8 is divided in anterior and posterior direction into two halves to be placed in a flat state, the stem 8 comprises the following structural elements made from FRP: an upper outer shell 4U, a main structure upper half 3U, a main structure lower half 3L and a lower outer shell 4L, and is integrated into one piece by stacking the FRP structural elements and applying heat and pressure to the FRP structural elements to melt resins impregnated in the FRP structural elements. Each of the upper and the lower shells is a curved prepreg sheet formed by impregnating carbon fibers arranged at angle of ±45 degrees with a thermoplastic resin, and each of the main structure upper and lower halves is an evenly stacked part in which prepreg sheets formed by impregnating carbon fiber with a thermoplastic resin are stacked. Overlapping sections 5 of the upper and the lower outer shells are formed such that the left and right portions of a main structure 3 formed by integrating the main structure upper and lower halves 3U, 3L have no stepped outer surfaces.

With the prepreg sheets forming each of the halves 3U and 3L of the main structure, the sheets 7M having carbon fibers arranged at angle of 0/90 degrees and the prepreg sheets 7N having carbon fibers arranged at angle of ±45 degrees are alternately stacked as shown in FIG. 5, giving pseudo-isotropy to each of the main structure upper and lower halves. As clear from FIG. 11(c) to (e), the shell 4 has a film on the surface thereof which is formed by melting resin compound 6.

As shown in FIG. 6, each of flat surfaces of the prepreg sheets evenly stacked in the main structure upper and lower halves 3U and 3L is parallel to a plane both containing a longitudinal reference line 8a linking a center 1a on the surface of upper end of a neck 1 for supporting the spherical joint and a center 2a in the end of diaphysis of the stem, and being on a line 7S toward the direction giving the least loss of shearing load acting on the stem.

Each of flat surfaces of the prepreg sheets evenly stacked in the main structure upper and lower halves 3U and 3L, as shown in FIG. 19, may be parallel to a plane both containing a longitudinal reference line 8a of the stem and is on a line 7T toward the direction minimizing the number of sheets to be stacked.

In producing any type of the artificial hip prosthesis stems described above, after stacking the FRP structural elements in the mold, the whole mold containing the FRP structural elements is entirely wrapped in a bag 12 made of heat resisting resin film (see FIG. 10(a), for instance). A vacuum is kept in the bag made of heat resisting resin film while heat and pressure are applied to the mold.

Effect of Invention

According to the present invention, the stem comprises the following structural elements made from FRP materials: an upper outer shell, a main structure upper half, a main structure lower half, and a lower outer shell, and by stacking these FRP structural elements and applying heat and pressure thereto to melt resins impregnated in each of the elements, the FRP structural elements are integrated into one piece as a stem. Each of the upper and outer shells is a thin prepreg sheet formed by impregnating carbon fiber with a thermoplastic resin, enabling the air voids occurring during the process of forming to be easily removed in spite of the fact that the sheet is curved in shape. Since the carbon fibers are arranged at angle of ±45 degrees, the shearing load, which acts larger on the stem as it is closer to the surface of the stem, may be received on the fibers arranged to be equivalent for the direction of the load and consequently the outer shells are very useful for reducing the shearing load reaching the resin sheets evenly stacked.

Furthermore, the shells, functioning as a hoop, have thick parts on the left and right sides of the main structure, which is described below, enabling the stem to maintain strength, proof stress and rigidity which an FRP-made stem formed merely by stacking FRP materials may not obtain, and accordingly the problems may be resolved which are caused when the internal structure covered with the shells is an evenly stacked part. The thin outer shells will fit the mold perfectly, as mentioned above, so that the stem will have accuracy in shape and size.

The main structure upper and lower halves are evenly stacked parts in which prepreg sheets formed by impregnating carbon fiber with thermoplastic resin are stacked, consequently as many air voids as possible left in the main structures may be removed. The overlapping sections of the upper and lower outer shells are to be formed on the left and right portions of the integrated main structure so as to reinforce the portion where the heaviest shearing load acts. The shearing load is transmitted at the thick overlapping sections and consequently a hoop effect will be increased in spite of the fact that the rest of the shells are thin. The inside structure of the stem is tightly held by the shells, enabling the property of keeping the shape of the stem close to the shape of a metallic stem.

The overlapping sections of the upper and the lower outer shells are formed so as to have no stepped outer surface of the stem, and consequently undesired unevenness will not be formed on the surface of the stem. With a cement stem, the advantage exists that an adhesive treatment for cement may be given uniformly on the surface of the stem. And with a cement-less stem, the advantage exists that a treatment may be effectively given of medicament for spongiosa bone growth, such as hydroxyapatite, on the surface of the stem. The stem may fit in the medullary cavity with little inclination, resulting in the improvement in fit and fill of the stem in the medullary cavity.

The structure of the main structure upper and lower halves in which the prepreg sheets having carbon fibers arranged at angle of 0/90 degrees and the prepreg sheets having carbon fibers arranged at angle of ±45-degrees are alternately stacked, promotes the pseudo-isotropy of each main structure upper and lower halves. The direction of the fibers at the cut ends meet to the tangential lines of the periphery of the layers at right angles, acute angles and obtuse angles, so that the layers may have neither cracks of cured resin nor the separation of resin from fibers. The fibers of the layers are engaged with the fibers of the outer shells to promote integrating the internal and external structures of the stem.

Covering the whole surface of the outer shell with a thin film made of melted PEEK resin compound may prevent the carbon fibers in the outer shell from appearing, so that the carbon fibers will not contact with the wall of the medullary cavity. Even if the carbon fibers are cut into small pieces in the shell, the thin compound film prevents the pieces from moving into and floating in the medullary cavity.

Each of the flat surfaces of the prepreg sheets evenly stacked in the main structure upper and lower halves is parallel to a plane which is on a line toward the direction giving the least loss of shearing load, i.e., a plane to resist the moment at the maximum, enabling the stem to have the maximum resistance against the moment caused by the load acting on stem. The adhesiveness among the sheets is improved owing to the flat surfaces of stacked sheets, which promotes the durability of the neck that receives heaviest load in the stem.

Each of the flat surface of the prepreg sheets evenly stacked in the main structure upper and halves is parallel to a plane which is on a line toward the direction minimizing the number of sheets to be stacked, as a matter of course, the sheets to be used can be decreased in number, resulting in reducing the labor required for forming.

In producing any type of the artificial hip prosthesis stems mentioned above, after stacking the FRP structural elements in a mold, the mold is entirely wrapped in a bag made of heat resisting resin film. Thus, the FRP structural elements in the mold may adhere to each other by keeping a vacuum in the bag made of heat resisting resin film while heat and pressure are applied to the mold. Even if the elements do not contact the contour of the cavity well or slightly extrude from the cavity before closing the mold, the elements are contained in the mold spontaneously during the curing operation, thereby the stem can be formed which is identical in outer shape to the cavity of the mold.

BEST MODE FOR CARRYING OUT THE INVENTION

Figure 1:
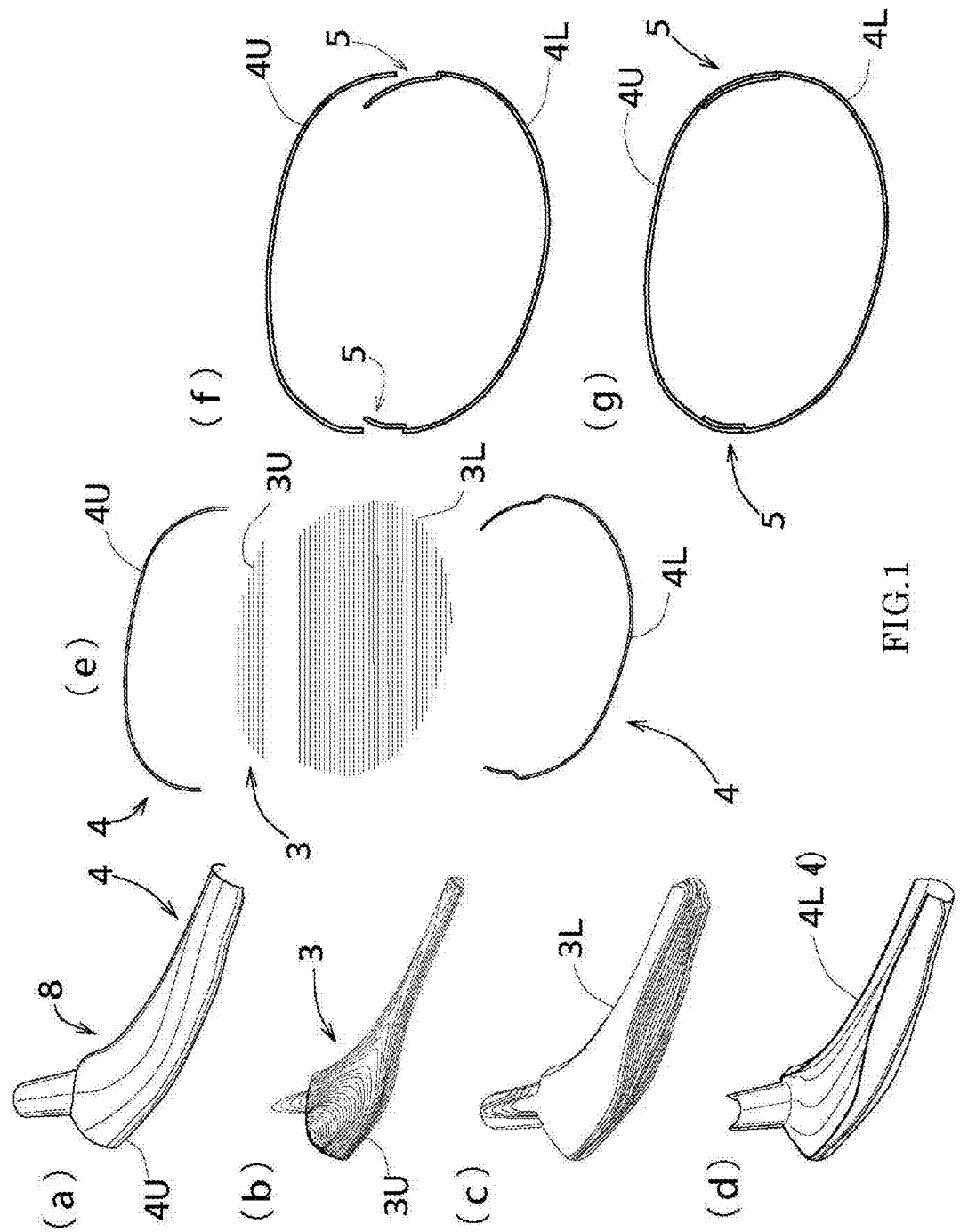
FIGS. 1(a)-1(g) are exploded views of a structure of composite prosthetic hip according to the present invention.

Referring to the drawings showing some embodiments, a structure of an artificial hip prosthesis stem and a method for producing the stem according to the present invention are disclosed as follows: The present invention is applied to a stem used as a prosthesis so as to restore the function of femur whose caput is broken due to a traffic accident or the like and the function of walking by reinforcing the femur which declines in rigidity due to osteoporosis. An artificial hip prosthesis stem is installed in the femur by inserting the stem into a hollow previously made from the epiphysis to the diaphysis of the femur. Two major methods are currently known to secure the stem in the femur; a method of using cement milk previously filled in the hollow, and a biomaterial method of using bone growth that spongiosa gradually fills up the space between the hollow and the stem to unite the stem and the femur without using cement. The main object of the present invention is to provide FRP stem without air voids and is applicable to both the methods as well.

Figure 2:
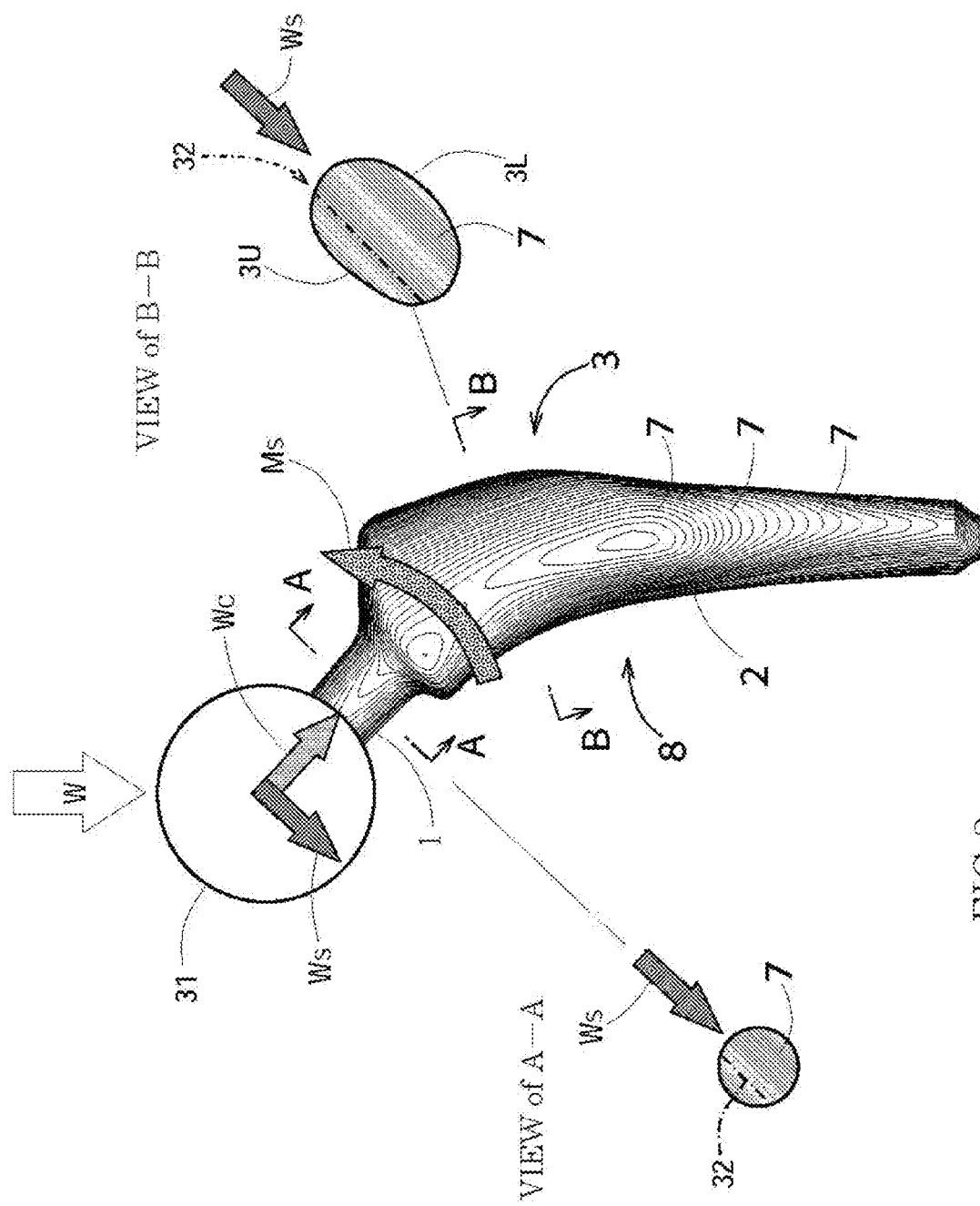
FIG. 2 is a view for explaining the load acting on the stem.

FIG. 1 is an exploded figure illustrating a structure of the artificial hip prosthesis stem according to the present invention, wherein a main structure 3 consisting of a neck 1 and a body 2, shown in FIG. 2, is made of evenly stacked FRP materials. The main structure comprises four structural elements, an upper outer shell 4U, a main structure upper half 3U, a main structure lower half 3L and a lower outer shell 4L as shown from (a) to (d) of FIG. 1. The stem is inserted in a femur with roughly substantially standing posture thereof, but for the sake of convenience for the stem in FIG. 2, as an example for a left femur, is placed in a flat state of the stem divided in anterior and posterior direction into two parts, i.e., the stem 8 is placed in a flat state with the anterior side thereof to be down and with the posterior side thereof to be up, as shown in FIG. 1.

More particularly, the stem may be obtained by stacking the structural elements: the upper outer shell, the main structure upper half, the main structure lower half and the lower outer shell, and applying heat and pressure to the structural elements by means of autoclave to melt the resin impregnated in each structural elements, and cooling them to be integrated into one piece. As a fiber woven in the structures, the carbon fiber is used which is tough and harmless to the human, thermoplastic resin such as PEEK resin or poly ether imid, which is also harmless to the human, is used as the matrix in order to keep the preferable shape of the stem. In order to melt the resin, a circumference temperature of approximately four hundred degree Celsius is required, even to soften it, heating it up to a temperature of more than three hundred degree Celsius is indispensable.

Figure 3:
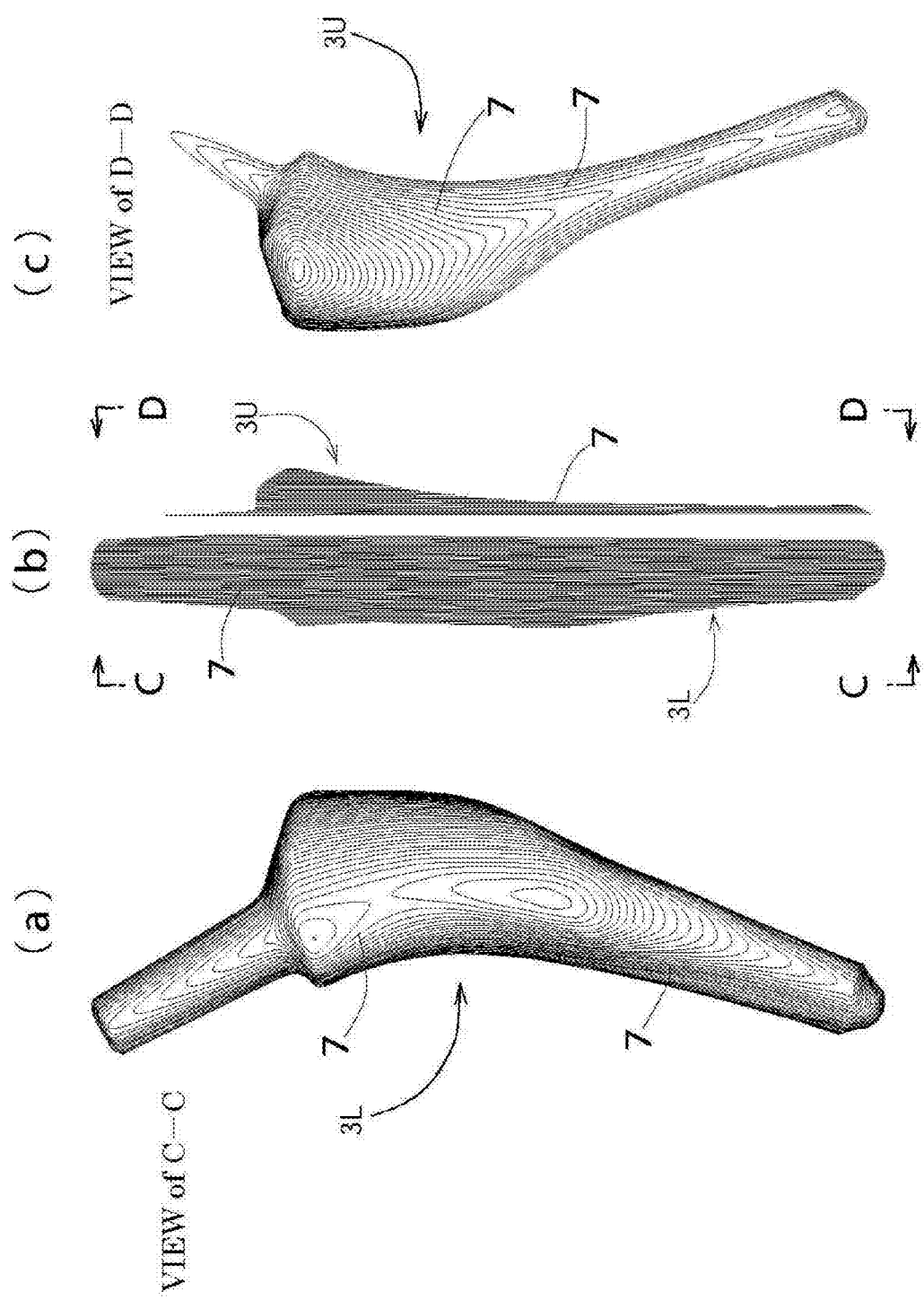
FIGS. 3(a)-3(c) are diagrammatic illustrations of the prepreg sheets evenly stacked in the stem.
Figure 4:
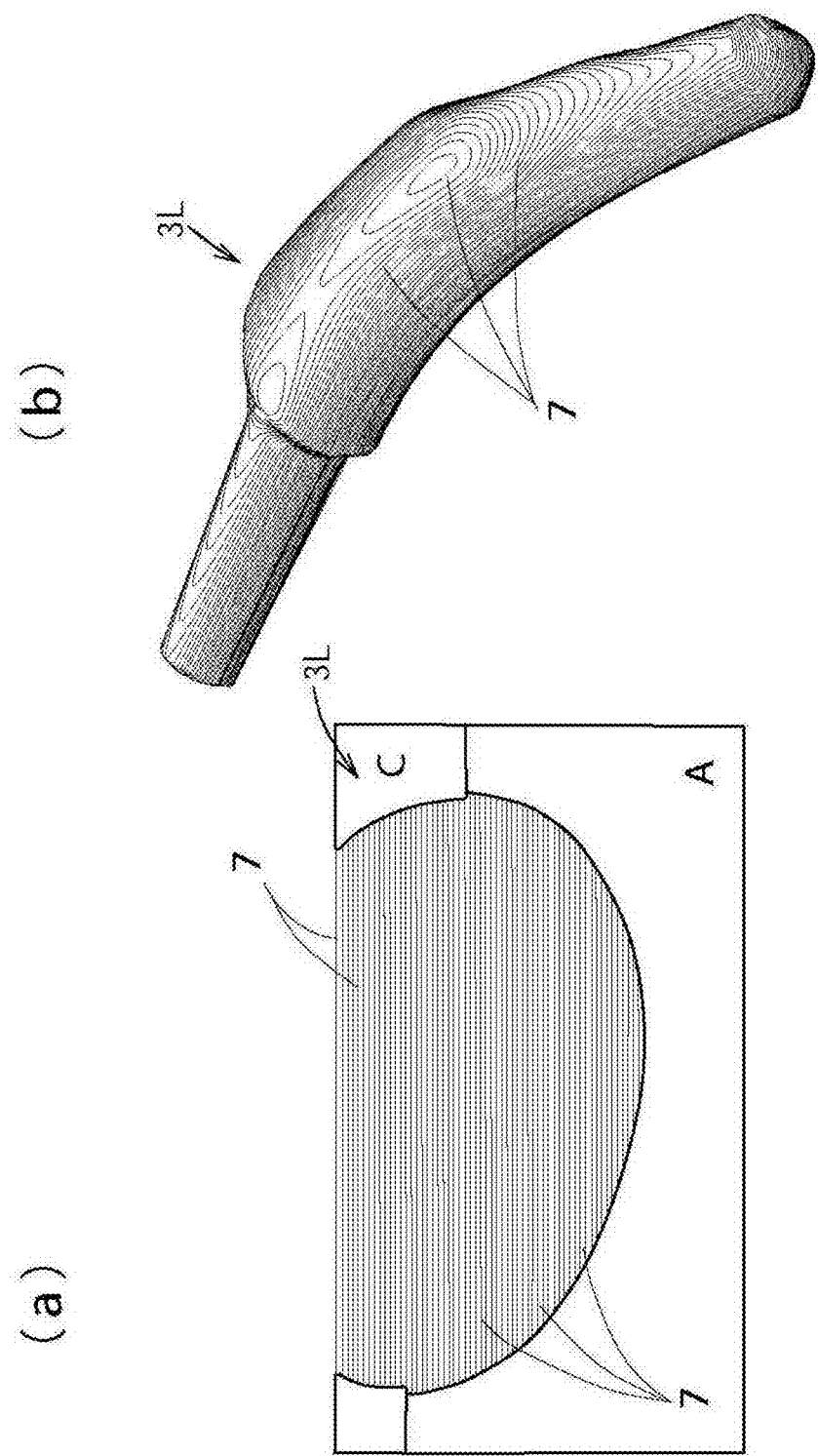
FIGS. 4(a)-4(b) are diagrammatic illustrations of the prepreg cutting sheets evenly stacked in the mold.
Figure 5:
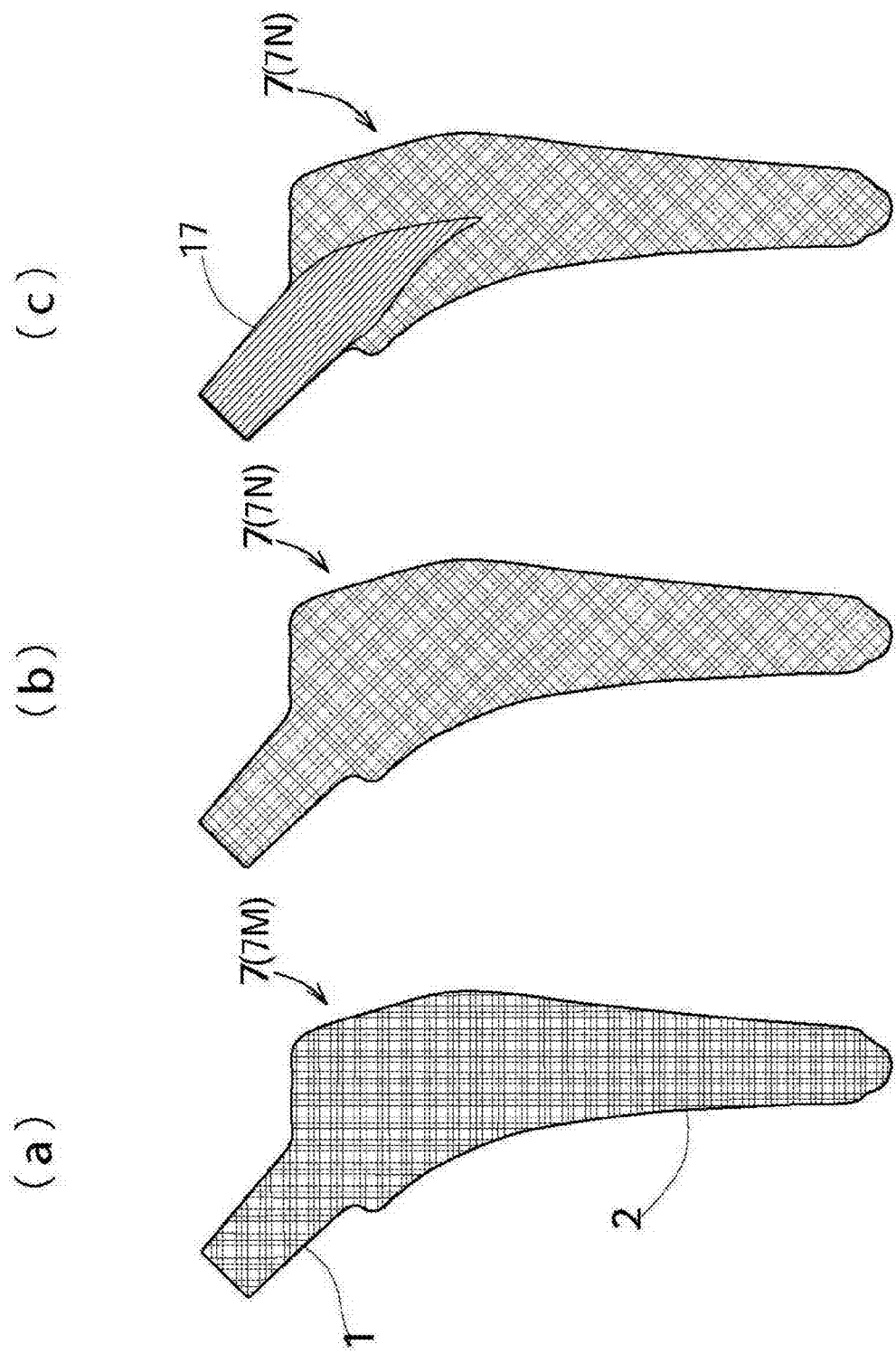
FIGS. 5(a)-5(c) are views of the surface of the prepreg cutting sheets evenly stacked for forming the main structure, which shows the modification of arrangement of the carbon fiber.

Each of the outer shells 4 is a curved prepreg sheet 15 formed by impregnating carbon fibers arranged at angle of ±45 degrees with a thermoplastic resin, which is mentioned below. Each of the main structure upper and lower halves 3U and 3L is an evenly stacked prepreg cutting sheets 7 formed by impregnating carbon fiber with a thermoplastic resin, as mentioned below in FIG. 3 and FIG. 4. Two kinds of the prepreg sheets are used of which woven cloth are 7M having carbon fibers arranged at angle of 0/90 degrees and 7N having carbon fibers arranged at angle of ±45 degrees, shown in FIGS. 5(a) and (b). Alternately laminating the prepreg sheets 7M and 7N enables each of the main structure upper and lower halves to have pseudo-isotropy. Incidentally, applying the prepreg sheet 17 having the one-way arranged carbon fiber to the neck part of the prepreg cutting sheets having 7N having carbon fibers arranged at angle of ±45 degrees, shown in FIG. 5(c), may realize the reinforcement in the axial direction of the stem. Each of the figures from (a) to (c) is an illustration of the prepreg sheets to be used for the widest part of the stem.

Each of the upper outer shell 4U and the lower outer shell 4L mentioned above is a curved thin layer to wrap up the main structure 3U and 3L, as the upper and lower halves of the main structure shown in FIG. 1(e). The curved thin layer is formed by heating the prepreg sheet 15 (see FIGS. 7(b) and (c) mentioned below) to soften it, which is not flexible at room temperature, and spreading it in the cavity of the mold to press against the surface of the cavity before it gets solid. Meanwhile the air remaining among sheets is squeezed out of the structures to prevent the air voids from occurring, which is realized due to the thin layer.

Due to the carbon fibers arranged at angle of ±45 degrees, the shearing load, the closer to the surface of the stem the larger the shearing load acts on the stem, may be received on the fibers arranged to be equivalent to the direction of the shearing load, and consequently the outer shells contributes to the reduction of the shearing load reaching the resin sheets evenly stacked. The upper outer shell 4U is secured to the lower outer shell 4L to form the overlapping section 5 shown in FIG. 1(f), the integrated main structure 3 is finally made to be smooth without a stepped outer surface on the left and right portions thereof, as shown in FIG. 1(g).

It is preferable for the outer shell to have a film to cover the surface thereof which is made from the resin compound 6, as shown in FIG. 7(a) mentioned below. The PEEK compound containing carbon fiber chips also will melt at the curing temperature. The film formed on the outer surface of the shell may keep the carbon fiber in the shell, thereby, preventing the carbon fibers from contacting with the inner wall of the medullary cavity, moreover, even if the fibers are broken in pieces, the resin film made of melted compound will keep catching the fiber pieces to prevent them from floating or scattering in the medullary cavity. When the carbon fiber is proved that it will not break, it is not necessary to form the film of melted resin.

Prepreg cutting sheets 7 are used for forming the main structure upper and lower halves 3U and 3L. Not only sheets fully impregnated with resin, but semi-prepreg sheets (or semi-preg sheets) insufficiently impregnated with resin may be usable, for curing enables any sheet to have the same quality of products. It is sufficient to select the sheet in consideration of either the relative difficulty in cutting the sheets into the prepreg cutting sheets 7 according to the contour lines or the financial costs for producing materials including the sheets, which vary with a degree of the curing.

Figure 6:
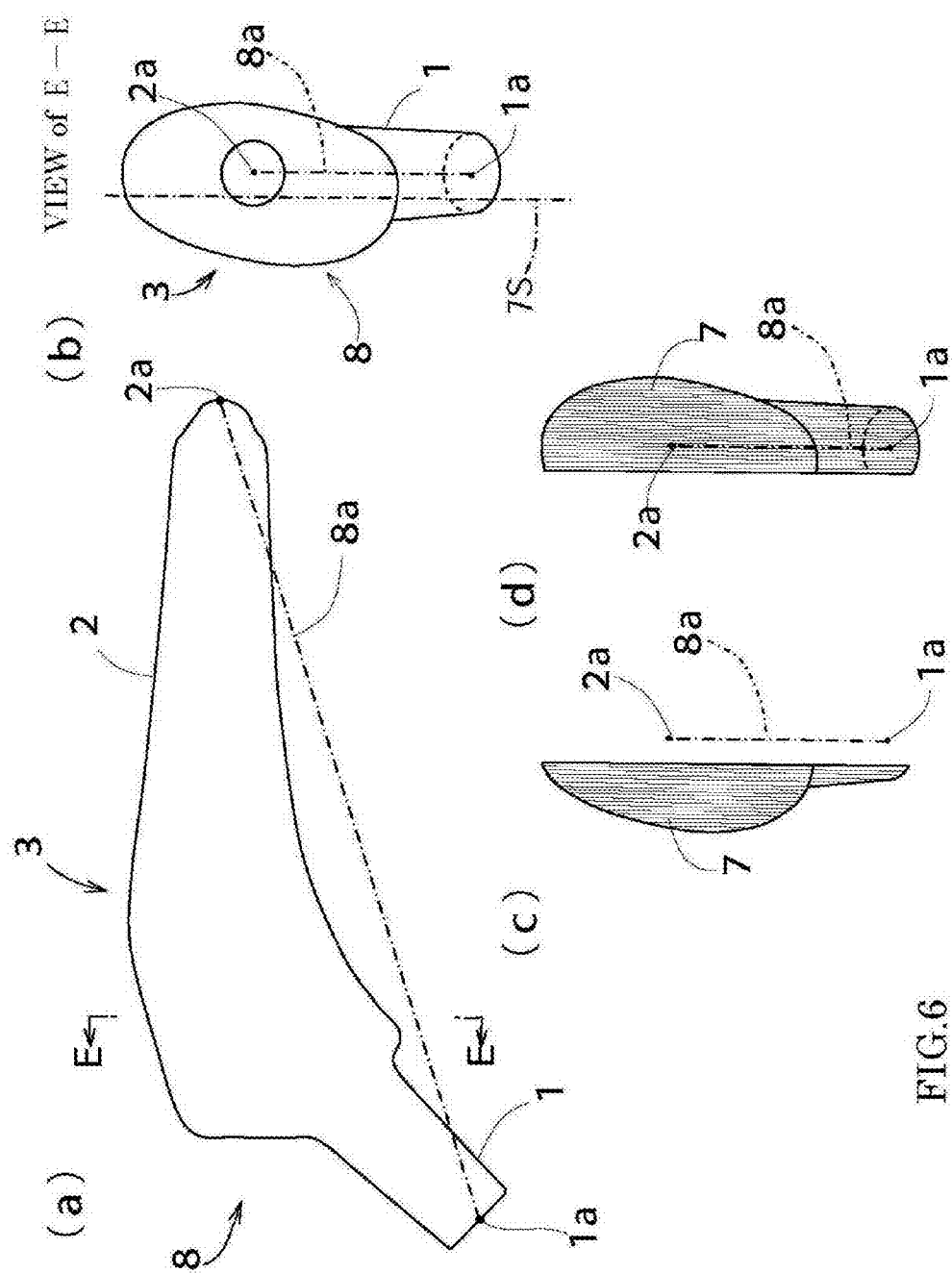
FIGS. 6(a)-6(d) are views for explaining the direction to extend the stacked prepreg sheets for the main structure upper and lower halves.

As shown in FIG. 6, each of flat surfaces of the prepreg cutting sheets 7 evenly stacked is parallel to the plane both containing a longitudinal reference line 8a of the stem 8 and being on a line 7S toward the direction giving the least loss of shearing load acting on the stem, i.e., theoretically zero. The longitudinal reference line 8a of the stem is a straight line linking a center 1a on the surface of upper end of the neck 1 supporting the spherical joint and a center 2a in the end of diaphysis of the stem. Thus the evenly stacked part may have the maximum resistance to the component $W_s$ in the direction of shear and the moment $M_s$ caused by the load W shown in FIG. 2.

In the left and right portions of the main structure, which is the vicinity of the upper end of the lower outer shell 4L overlapping the lower end of the upper outer shell 4U, i.e., the margin for overlapping sections of the upper and lower outer shells, as clear in FIG. 1(g), the prepreg cutting sheets 7 are used which have smaller outlines by a thickness of the shell. As mentioned later, numerical values based on secondary data are applied to NC cutting of the prepreg cutting sheets, which is obtained by subtracting one or two thicknesses of the shell from the outline data of the shell.

An artificial hip prosthesis stem made of composite material is composed as described above and formed in a method mentioned hereinafter, so that the stem can be obtained as a molded product whose main structure upper and lower halves 3U and 3L are evenly stacked parts in which prepreg cutting sheets 7 formed by impregnating carbon fiber with a thermoplastic resin are stacked. Air voids remaining in the main structure may be eliminated as many as possible. The overlapping sections 5 of the upper and lower outer shells 4U, 4L are formed on the left and right portions of the integrated main structure 3, meaning that the section on which the heaviest shearing load acts is effectively reinforced by the two-ply shell.

Figure 7:
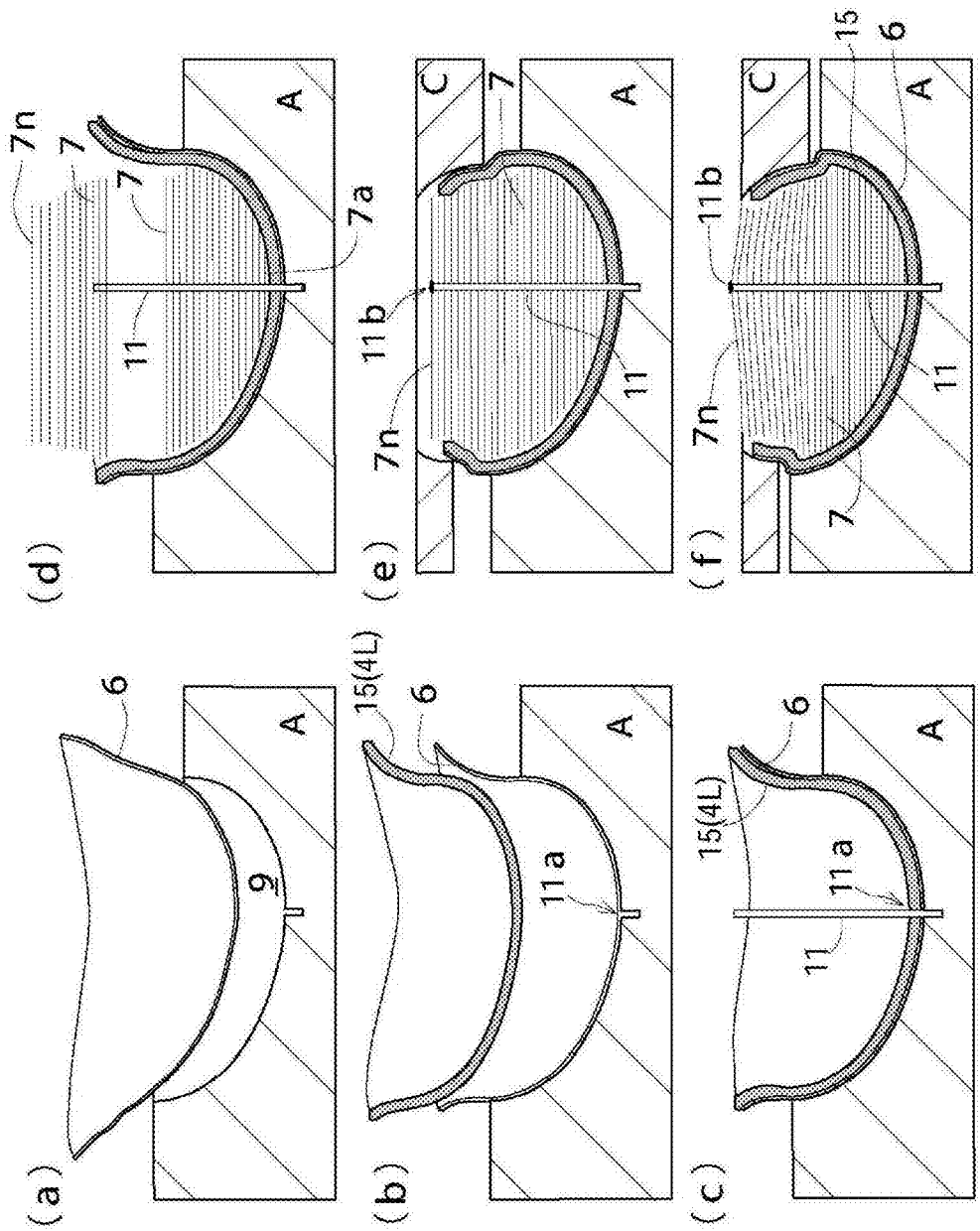
FIGS. 7(a)-7(f) show a flow diagram illustrating the first half of the process for forming the main structure lower half.

The process for forming the stem which is shown in FIG. 1(*a*)-(*d*), will be explained as follows by giving an example of the FRP structural elements 3La (see FIG. 10(*f*)) which is previously integrated with the lower outer shell 4L before integrating the main structure lower half 3L and the main structure upper half 3U. Referring to FIG. 7, a softened film of PEEK resin compound 6 is spread on the cavity 9 of the lower mold A, as shown in (a). This film has a thickness of, e.g., 0.5 millimeters and contains carbon five chips of several millimeters long, which is different from prepreg sheets 15 of 0.2 millimeters in thickness mentioned below.

The method for outlining the prepreg cutting sheets 7 stacked to form the main structure is mentioned hereinafter. From the shape of the stem to be applied to the patient, the outline is obtained of the main structure placed in a flat state every contour line by calculating. The prepreg sheets are cut in accordance with the contour lines by means of NC cutting machine. At the same time, a hole 10 for inserting a guide bar (see FIG. 9), mentioned below, is punched in the sheets. The hole is not always necessary but facilitates stabilizing of the prepreg sheets while the sheets are stacked. A rectangular bar is more useful than a cylindrical bar to prevent the prepreg sheets 7 from horizontally rotational slip.

Figure 8:
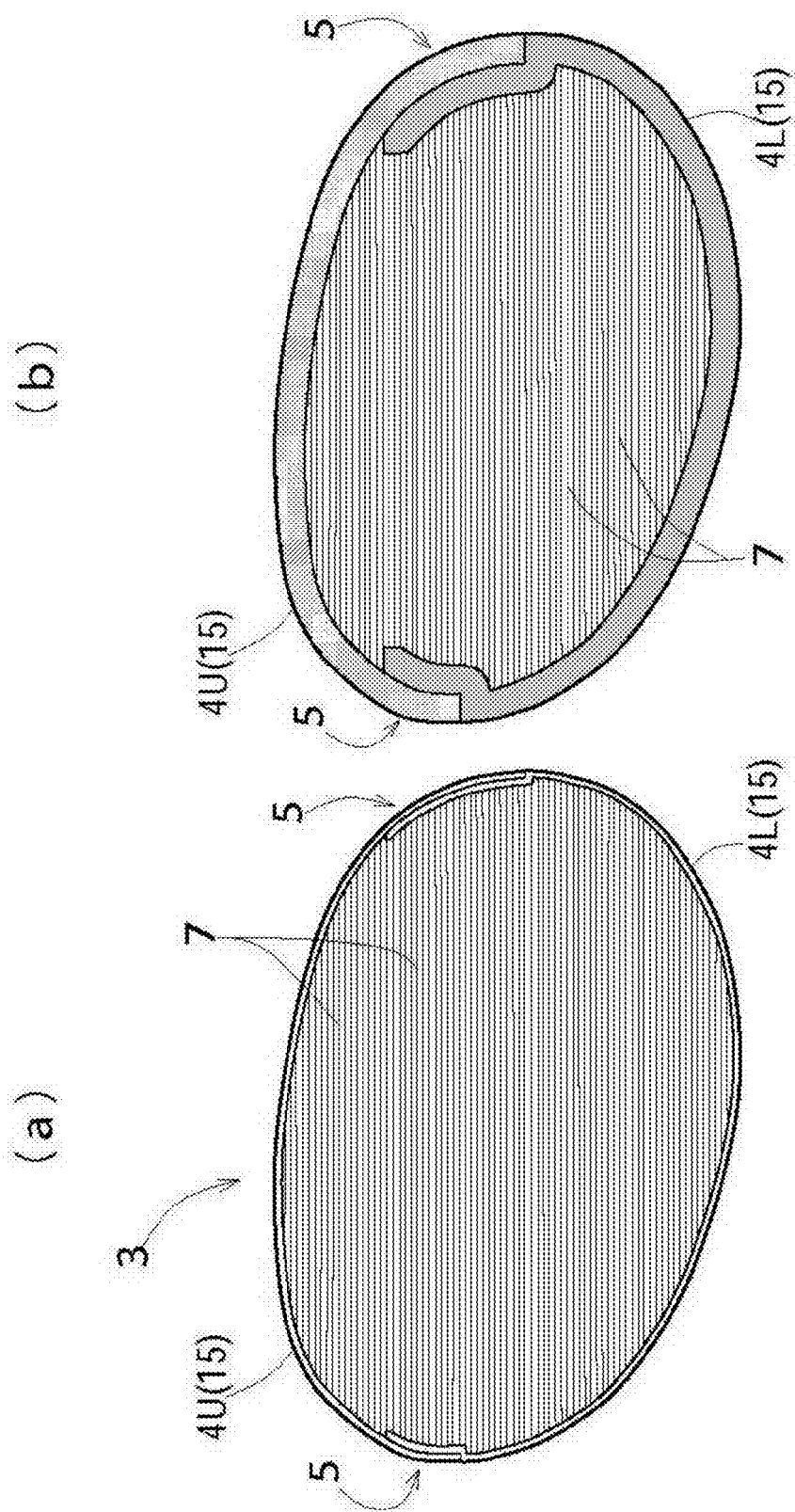
FIGS. 8(a) and 8(b) are views for explaining a way to illustrate the cross sectional structure of the stem.

As shown in FIG. 7(*b*), on the compound sheet 6 covering the cavity of the mold, the prepreg sheet 15 is spread which is formed by impregnating carbon fibers arranged at angle of ±45 degrees with PEEK resin so as to form the shell. The sheet is thinner than the compound sheet 6, as mentioned above, but the thickness thereof is shown to be thicker than the actual one in the figure so as to make clear the existence thereof in comparison with the compound 6 which becomes a thin film having little thickness. In the figures used for the subsequent illustrating the forming process, the shells will be illustrated to be thick as shown in FIG. 8 (*b*), although they should be illustrated to be thin as shown in FIG. 8(*a*).

Figure 9:
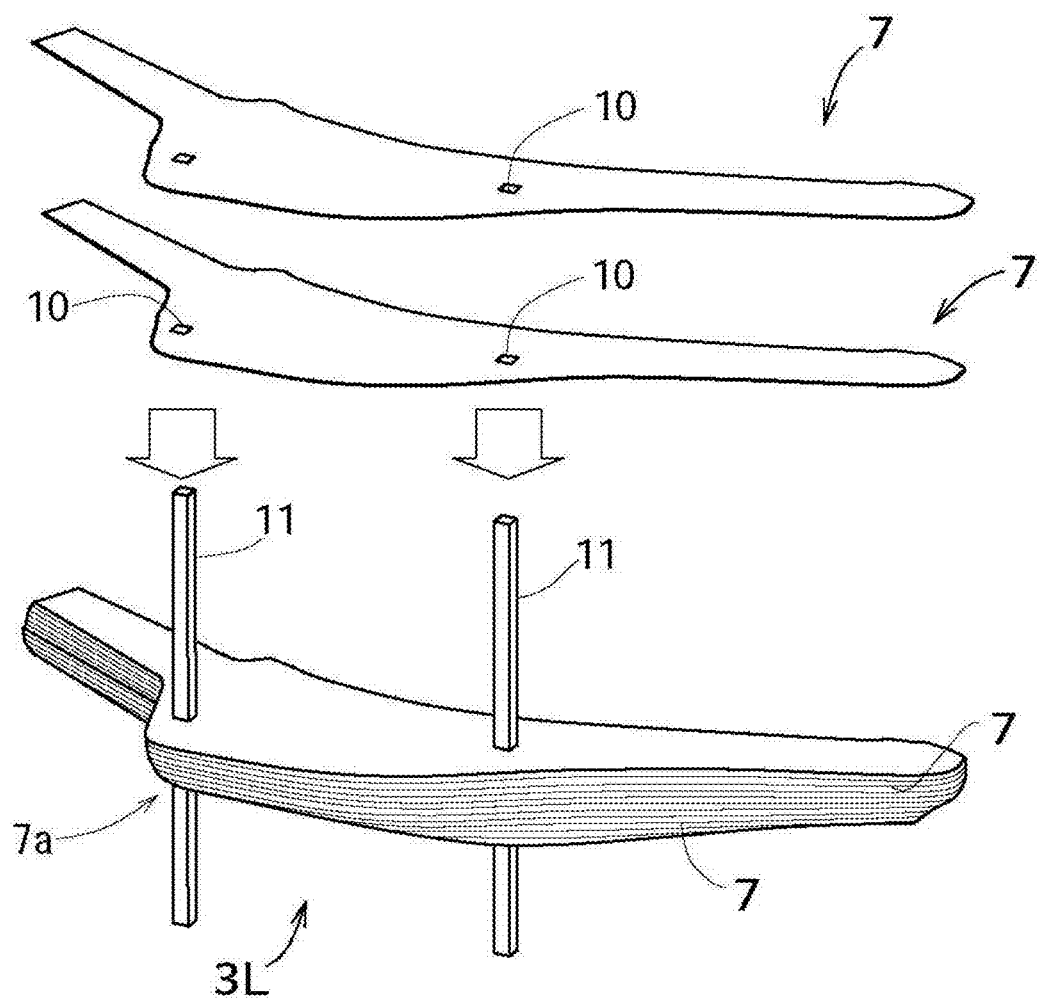
FIG. 9 is a schematic view of the guide bars made of resin and a group of the prepreg sheets being evenly stacked through which the guide bars pass.

While the compound sheet 6 and the initial prepreg sheet 15 are kept to be soft, a guide bar 11 made of PEEK resin is disposed in a hole 11*a* of the bottom of the cavity of the lower mold A, as shown in FIG. 7(*c*). This bar is useful in preventing the prepreg cutting sheet 7 from sliding while the sheets are stacked for forming the main structure, as shown in (d). The position of the guide bar 11 is determined at the point where it will certainly pass through the first sheet 7*a* of the main structure upper or lower half as shown in FIG. 9, and this will clearly appear from FIG. 7(*d*) as well.

The guide bar disposed at the point so as to pass through the first stacked sheet 7*a*, inevitably passes through every hole 10 of all the prepreg cutting sheets 7 stacked in the mold. If the prepreg cutting sheets should be preferably in position, the periphery thereof ought to be held by the cavity of the mold. Although thin plates, the prepreg cutting sheets are stiff at room temperature and often have flash on the periphery thereof when being cut out, therefore the sheets inevitably slip when they are stacked. The guide bar is usable to prevent the sheets from slipping mentioned above.

As shown in FIG. 7(*e*), the top sheet 7*n* is spot welded by resin 11*b* to the upper end of the guide bar 11 with an electric iron or the like, thereby the prepreg cutting sheets 7 may be prevented from being apart each other and increasing the volume thereof at room temperature. As shown in (f), even if the sheets 7 tend to be lifted in the mold before closing the mold, the bar will keep the posture of the stacked prepreg cutting sheets 7 preferable till the mold is completely closed as mentioned below.

Figure 10:
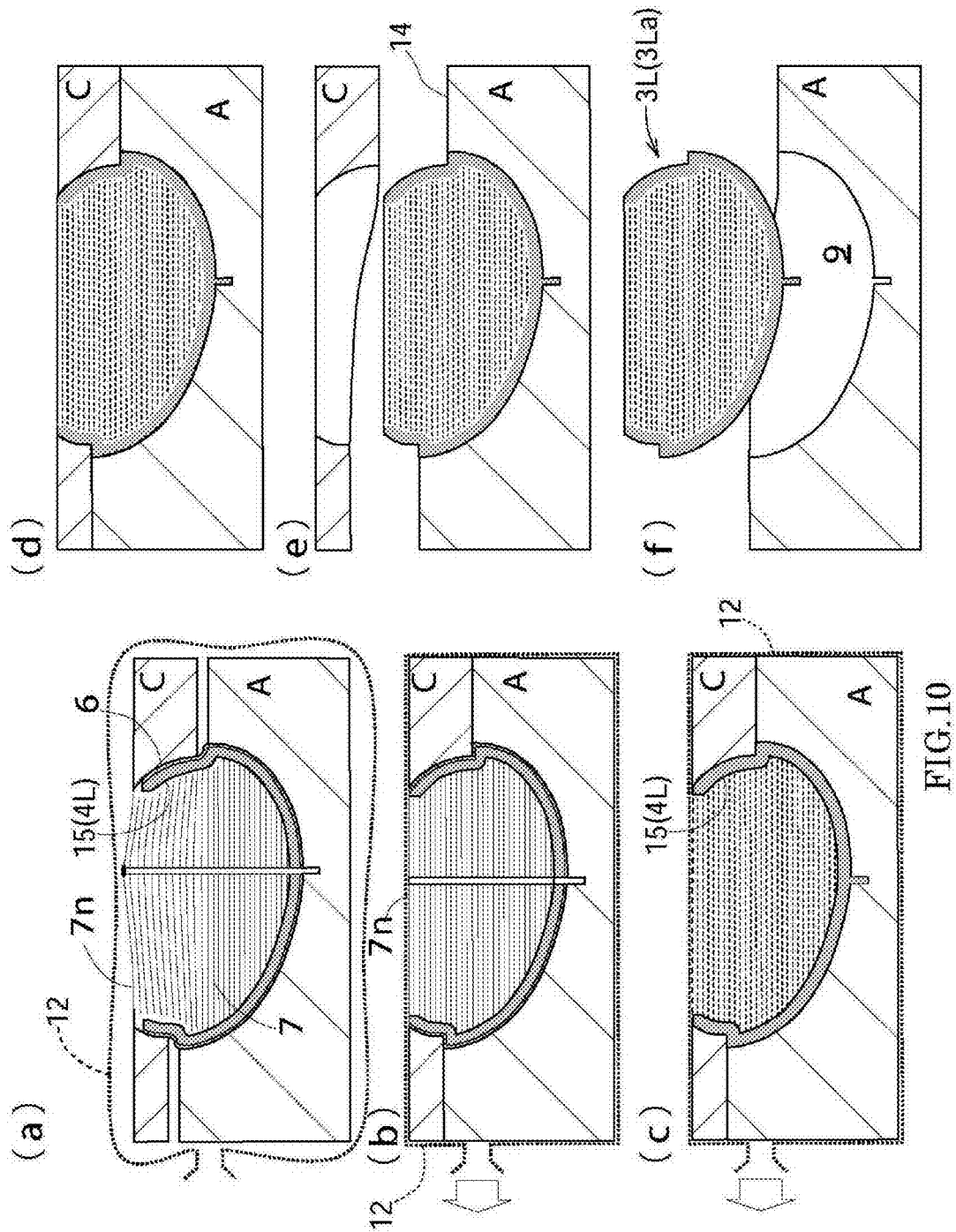
FIGS. 10(a)-10(f) show a flow diagram illustrating the latter half of the process for forming the main structure lower half.

As shown in FIG. 7(*f*), the prepreg cutting sheets 7 for the main structure lower half and the FRP structural elements 4L made by integrating the prepreg sheet 15 and the compound 6 for the lower outer shell are stacked in the molds A and C, the whole molds are entirely wrapped in the bag 12 made of heat resisting resin film, as shown in FIG. 10(*a*). The bag is made of film such as heat resisting polyimide resin film or the like whose melting point is higher than that of PEEK resin, so that it can keep wrapping the molds up throughout the curing operation. While the molds are heated and pressurized in autoclave, the compound sheet 6 melts to cover the prepreg sheet 15, the guide bar 11 melts to mix with the prepreg cutting sheets 7. The resins impregnated in the prepreg cutting sheets 7 will mix with the resins in the prepreg sheet 15, the guide bar will melt into the sheets to lose its shape as shown in (c), and the compound sheet becomes negligible in thickness. The prepreg cutting sheets melt to be integrated with the prepreg sheet 15 which is for forming the outer shell. The air in the bag is successively taken out to establish a vacuum, thereby the bag will tightly wrap the whole mold including the top sheet 7*n* which sticks out of the mold (see FIG. 10(*b*)), so that a part of the bag may function as the mold.

What should be mentioned previously, is that a middle mold C is used in FIG. 7(*e*). The main structure lower half 3La integrated with the lower outer shell as shown in FIG. 10(*f*) is not removable from a single mold. It is an obvious fact that the parting surface between the lower mold A and the middle mold C is selected on the widest part of the product, however, the main structure lower half 3L has the shape such that the widest part is in the middle thereof, so that the middle mold is indispensable in order to remove the main structure. The entirely close of two blocks as a set of a mold is made with the contact of two parting surfaces each other by vacuum contraction of the bag after all the PEEK resin in the molds melts up to begin decreasing in volume. Not only the vacuum contraction but also pressurizing the bag on the outside, in case of necessity, may promote the mold closing as multiplier effect.

Figure 11:
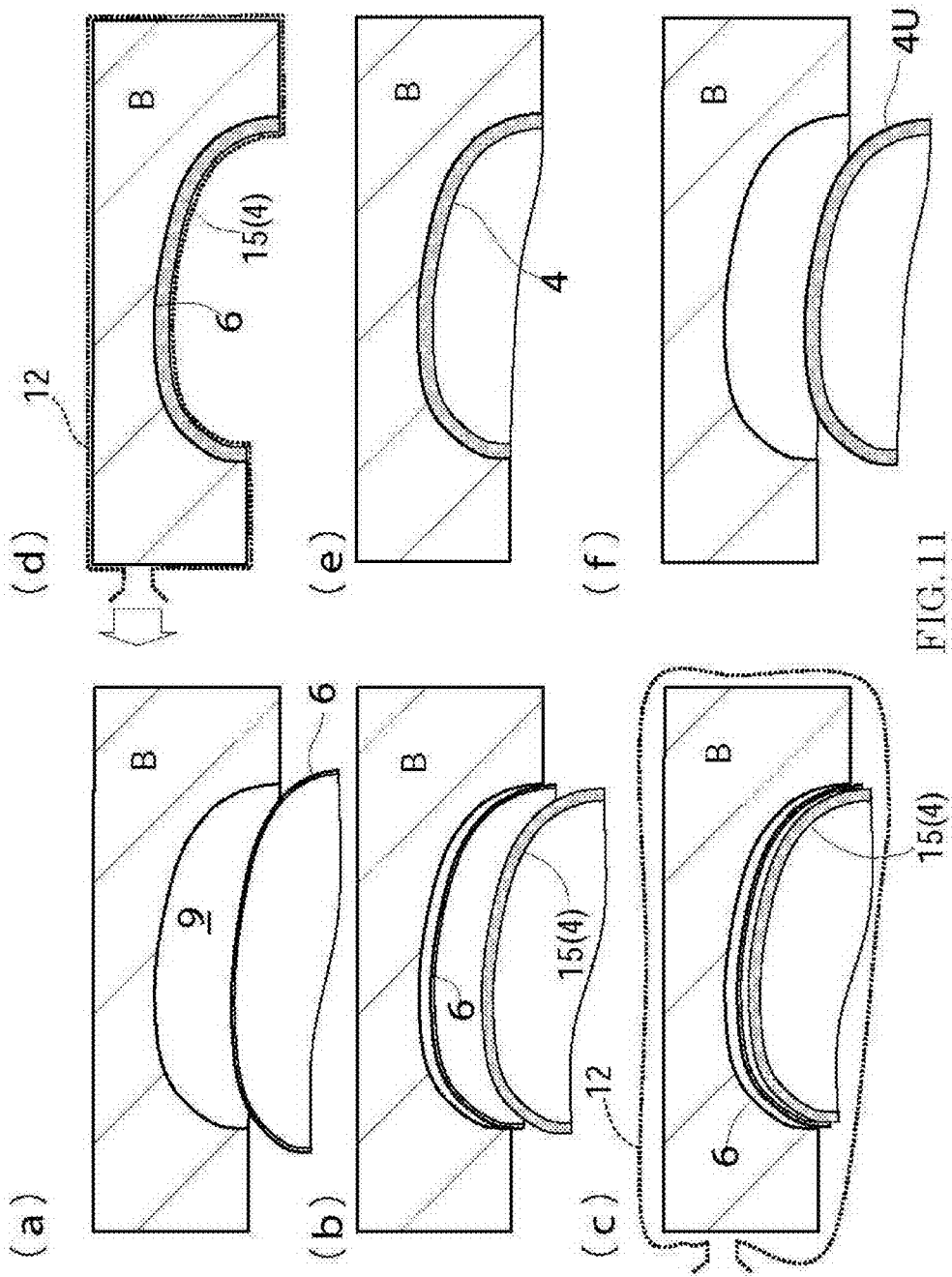
FIGS. 11(a)-11(f) show a flow diagram of forming the upper outer shell.

The process of forming the upper outer shell 4U and the main structure upper half 3U will be disclosed as follows: FIG. 11 shows the process of the upper outer shell, but (a) and (b) thereof are essentially the same as (a) and (b) of FIG. 7. They are illustrated upside down, contrary to the posture thereof in forming, which is easy to visually understand the process of forming the FRP structural elements by illustrating the upper outer shell according to the actual position of it. The mold for the upper outer shell is also used as the upper mold B mentioned below, wherein the prepreg sheets need not be stacked, so that at (c) the upper mold B is entirely wrapped in the bag 12 made of heat resisting resin film.

Figure 14:
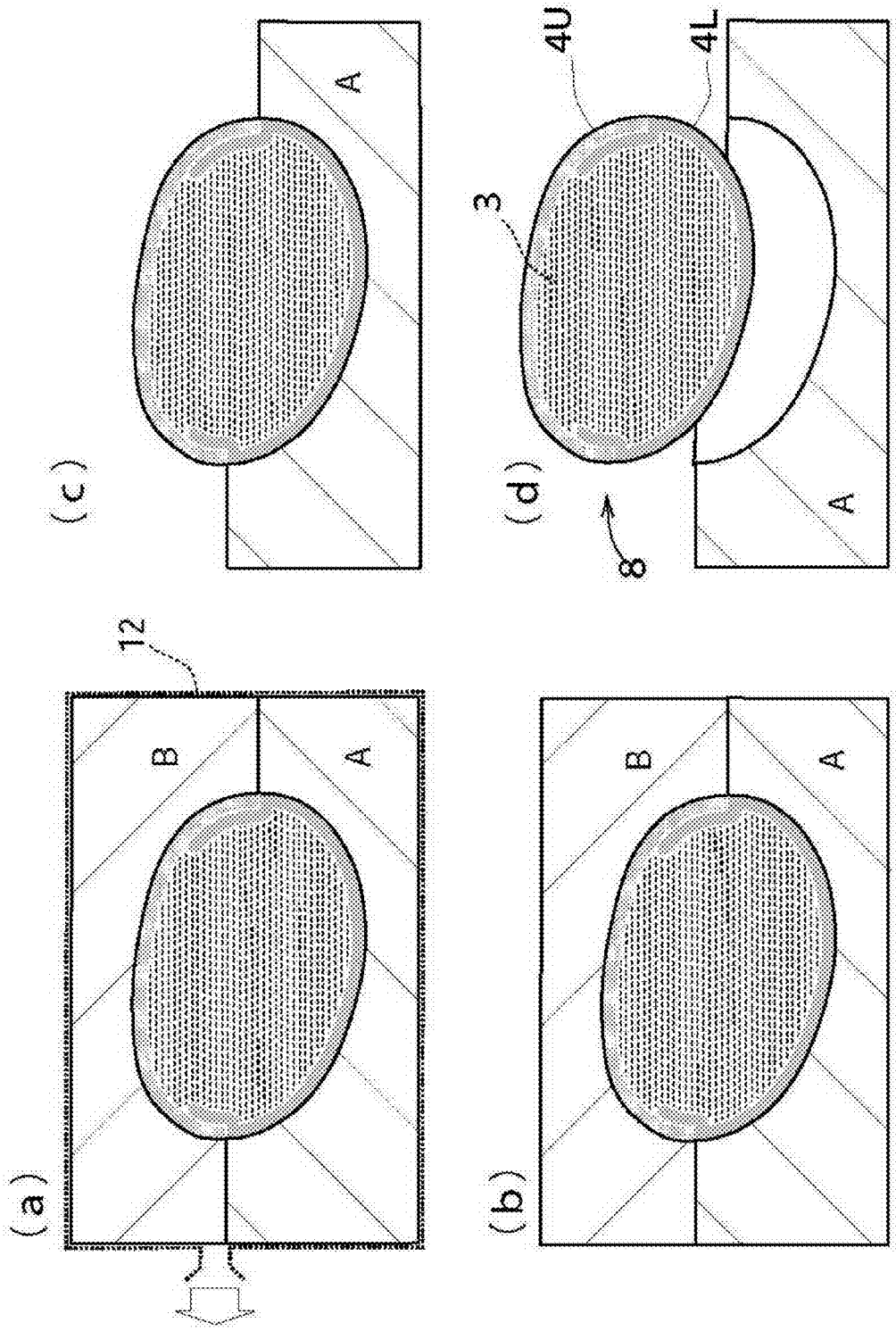
FIGS. 14(a)-14(d) show a flow diagram of the latter half of the process for the final assembling of the stem.

As shown in FIG. 11(*d*), the bag 12 will partly contact to the prepreg sheet for the outer shell by vacuum contracting. The compound 6 melts to be integrated with the prepreg sheet 15 so as to form the outer shell 4. Incidentally, the bag needs not perfectly contact to the prepreg sheet so far, for each of the compound sheet and the prepreg sheet is a curved sheet and still remains soft in (a) and (b). In the stage of FIG. 14 (*a*) mentioned below, the resin in the sheet will melt to have a shape in agreement with the mold. The upper outer shell 4U is removed from the mold in FIG. 11(*f*) after the process of FIG. 11(*e*) where the bag has already removed.

Figure 12:
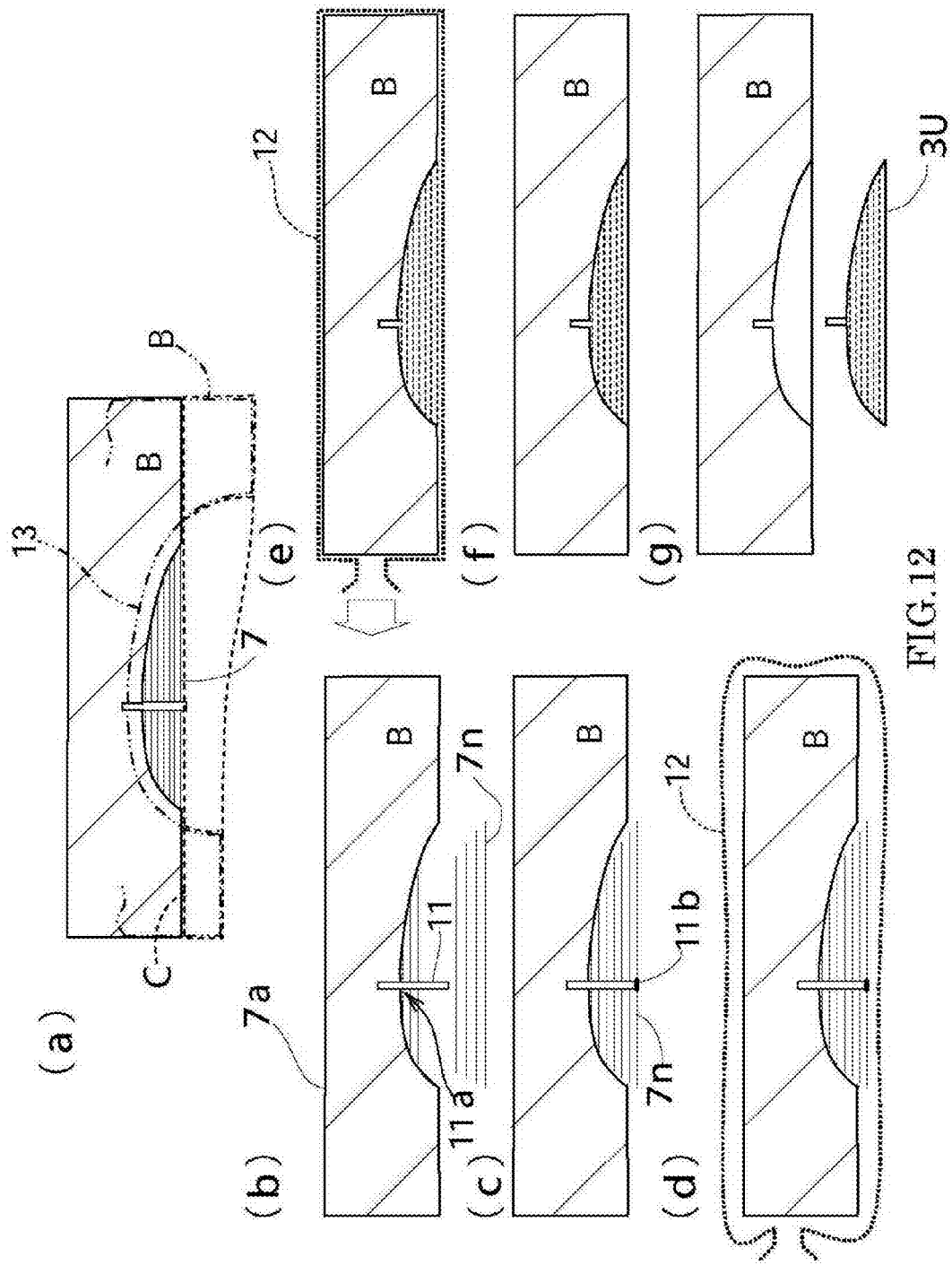
FIGS. 12(a)-12(g) show a flow diagram of forming the main structure upper half.

FIG. 12 shows the process of forming the main structure upper half 3U. This is formed as an independent FRP structural element, in a different process from the process of forming the main structure lower half 3La described in FIG. 10 (*f*).

Thus the size of the cavity of the mold B' is lessened by a thickness of the shell. The curved line 13 of two-dotted chain line in (a) shows the outward form of the upper outer shell, and the solid line shows the outward form of the main structure upper half 3L, accordingly the mold B' used in the figures farther than (b), can be used for neither forming the upper outer shell nor final assembling described below. When the main structure upper half is formed, the middle mold C shown in FIG. 7(*e*) is unnecessary, because the main structure upper half has the shape to be removed from the mold without dividing the mold. The bag is removed after curing, the main structure upper half is removed from the mold as illustrated from FIG. 12(*f*) to (*g*). The mold B' used herein has such a form, as shown in (a), that the middle mold C in FIG. 7(*e*) is removed from the upper mold B in FIG. 11.

Figure 13:
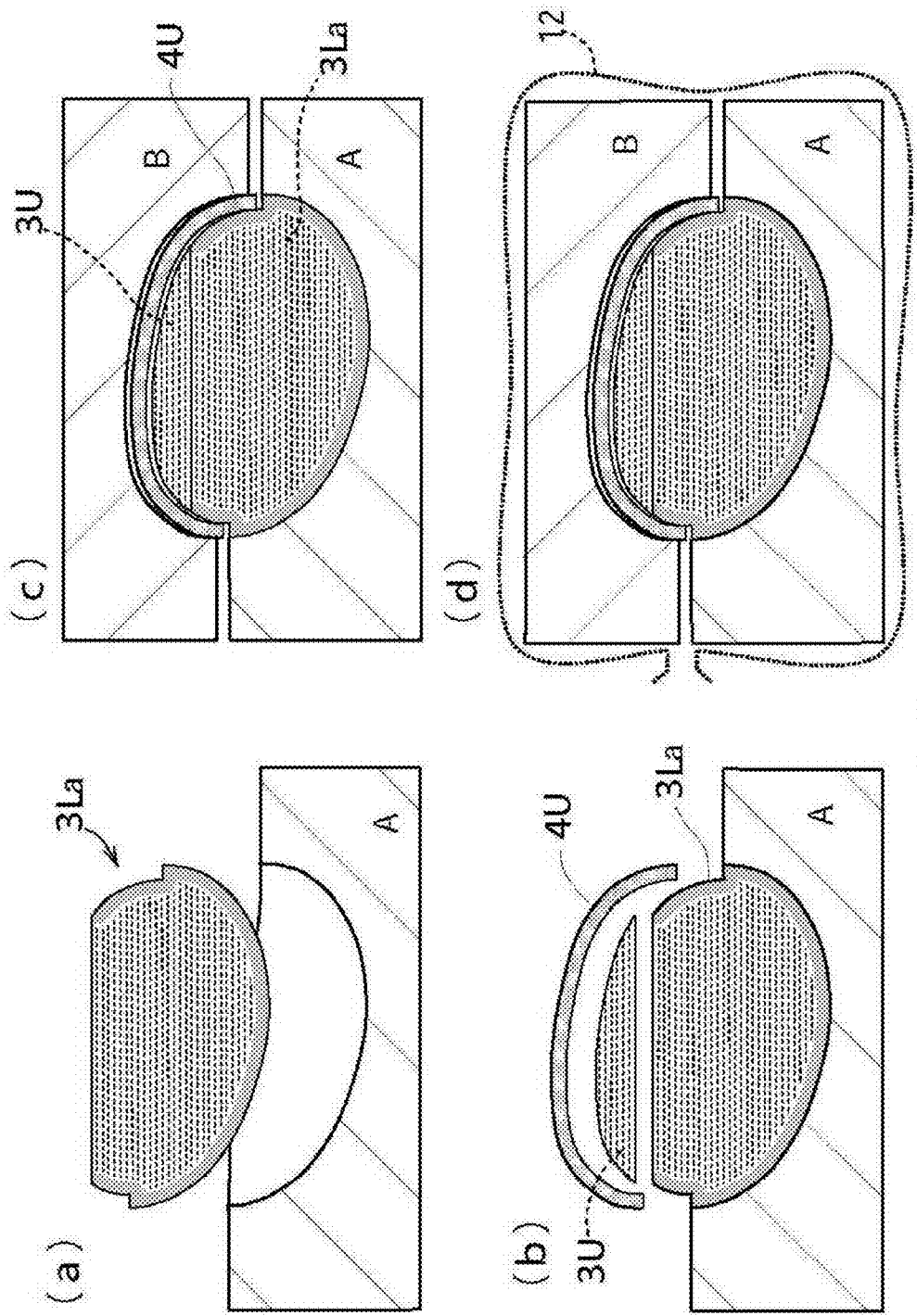
FIGS. 13(a)-13(d) show a flow diagram of the first half of the process for the final assembling of the stem.

Each of the FRP structural elements: the upper outer shell 4U, the main structure upper half 3U and the main structure lower half 3La having the lower outer shell mentioned above, is formed by the method explained above. After the process as shown from (a) to (d) of FIG. 13 and from (a) to (c) of FIG. 14, an integrated one piece may be obtained which is usable as the stem 8. The concept of handling technology in each process is essentially same as that of FIG. 7 and FIG. 10, where the upper mold B and the lower mold A are used. The upper mold B for forming the upper outer shell, and the mold A for forming the lower half with the lower outer shell are also used for the final assembling.

In the case that the stem comprises the four FRP structural elements: the upper outer shell 4U, the main structure upper half 3U, the main structure lower half 3L and the lower outer shell 4L, the lower mold A is usable for forming the lower outer shell as mentioned above, but in order to form the main structure lower half, the mold A' (not shown) is necessary whose cavity is lessened by a thickness of the shell, which is the same as forming the main structure upper half. In this case, not only the lower mold A' but the middle mold C' (not shown) will be indispensable, this is clear from FIG. 10(*e*). In the mentioned case that the stem comprises the three FRP structural elements: the upper outer shell 4U, the main structure upper half 3U and the main structure lower half with the lower outer shell 3La, it is sufficient to prepare four molds; the mold A and the mold C shown in FIG. 7 and the mold B shown in FIG. 11 and the mold B' shown in FIG. 12.

In the case that the stem comprises the four FRP structural elements: the upper outer shell 4U, the main structure upper half 3U, the main structure lower half 3L and the lower outer shell 4L, in addition to the four molds, the lower mold A' and the middle mold C' described above, six molds in total, have to be prepared, which is not shown in the figures. As far as the number of the molds concerned, in custom made stem, of course, decreasing the total number of the mold means that the stems can be manufactured at a lower cost than usual.

Figure 15:
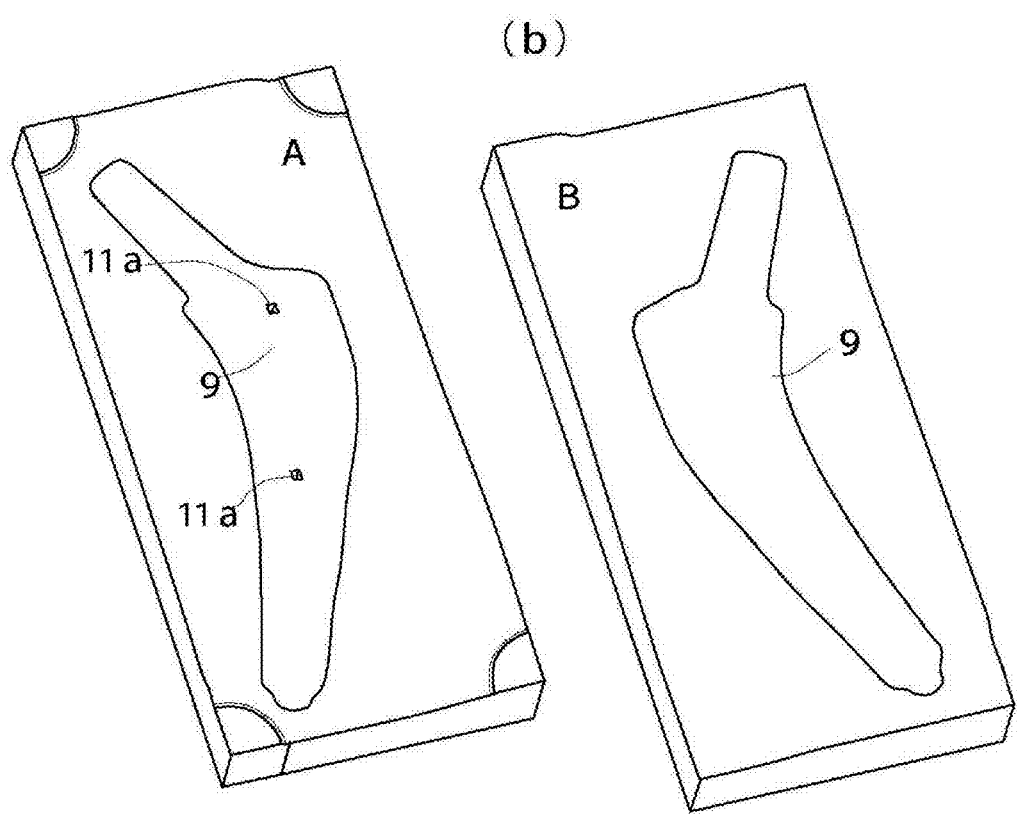
FIGS. 15(a) and 15(b) show a schematic view of the upper and lower blocks as a set of mold with their cavities being opened.

FIG. 15 is a schematic view of the upper and lower blocks as molds

Figure 16:
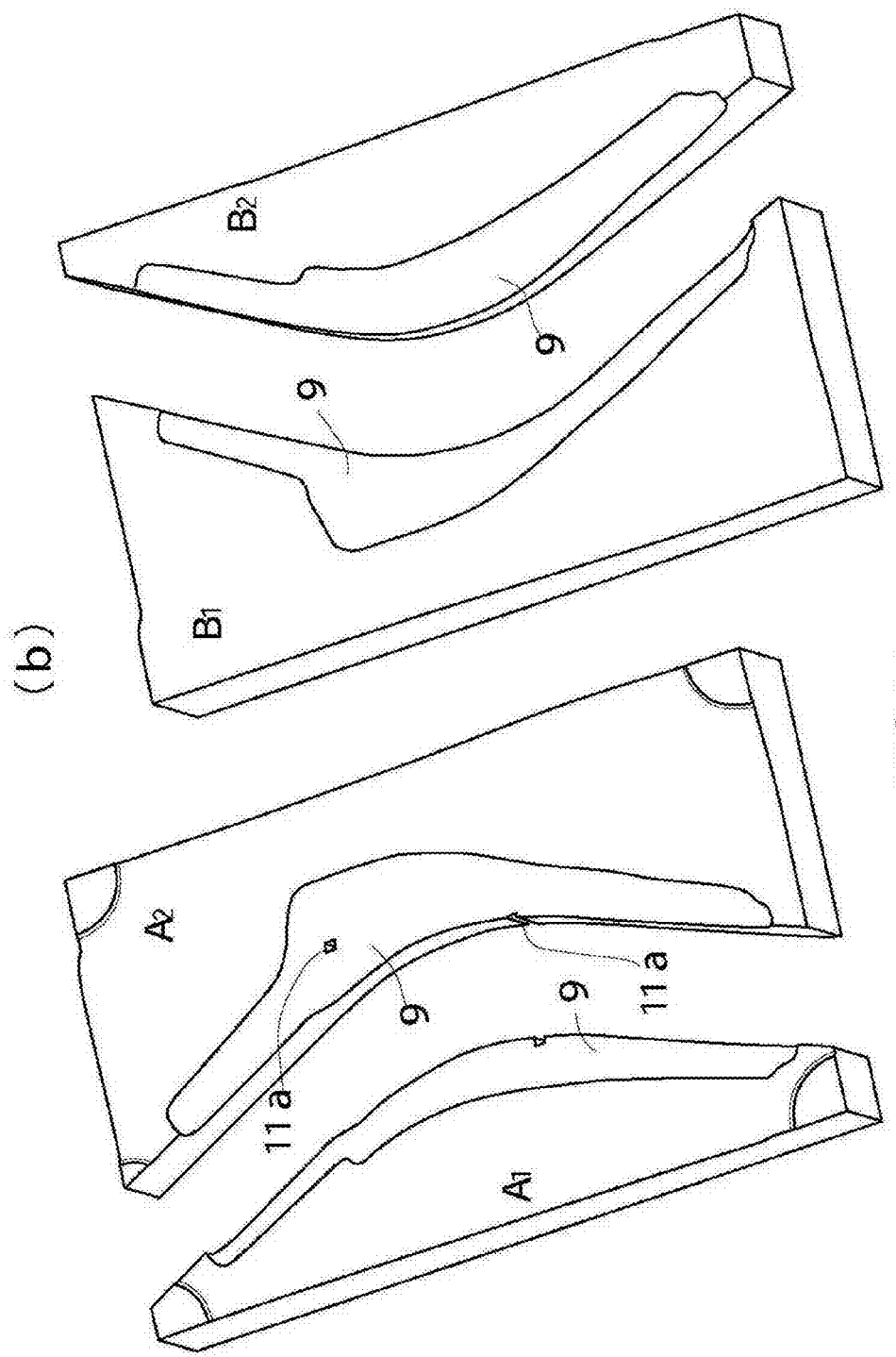
FIGS. 16(a) and 16(b) show a schematic view of the upper left, upper right, lower left and lower right blocks as a set of mold with their cavities being opened.
Figure 17:
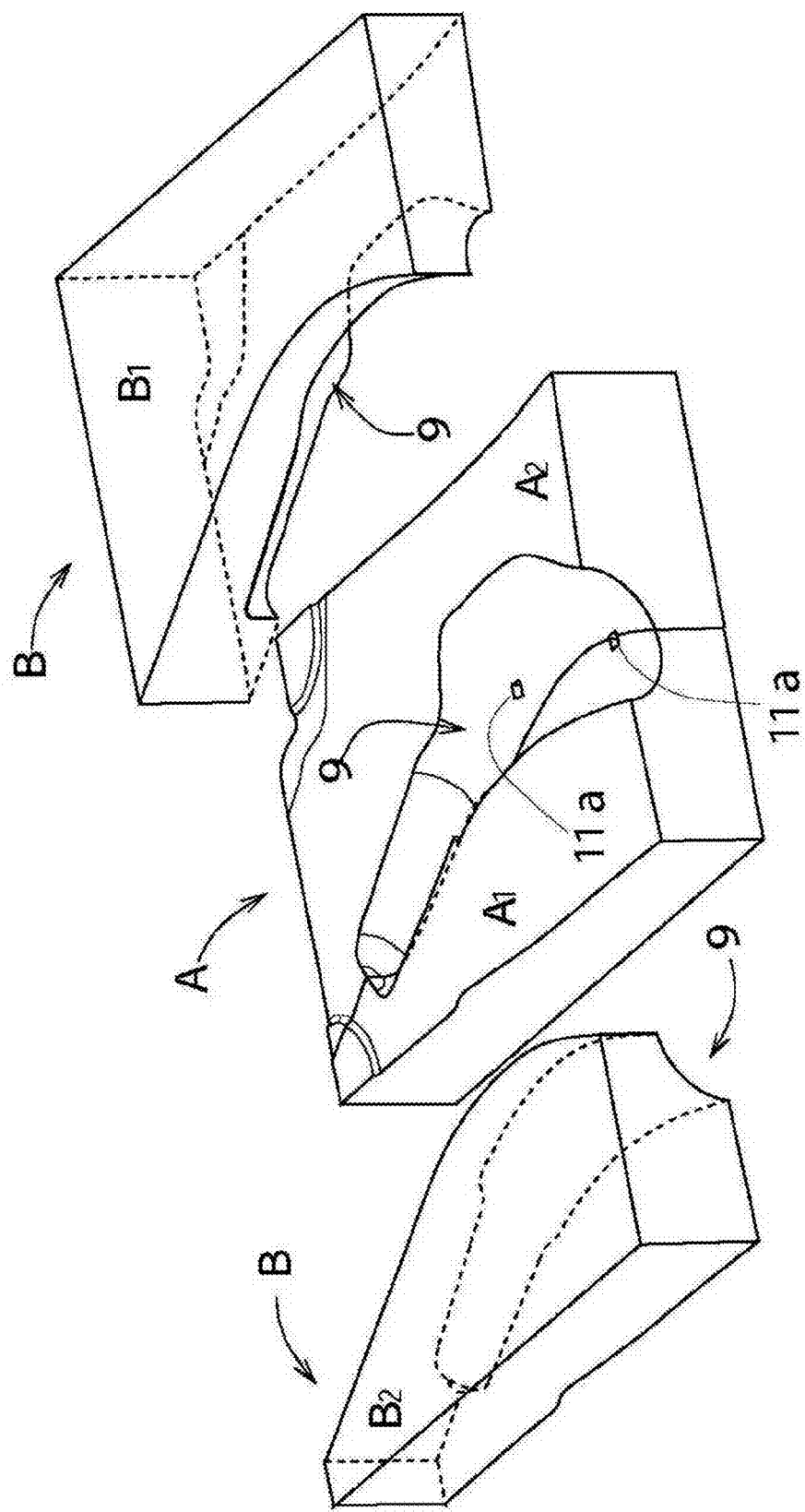
FIG. 17 is a schematic view of four blocks being assembled into a set of mold.
Figure 18:
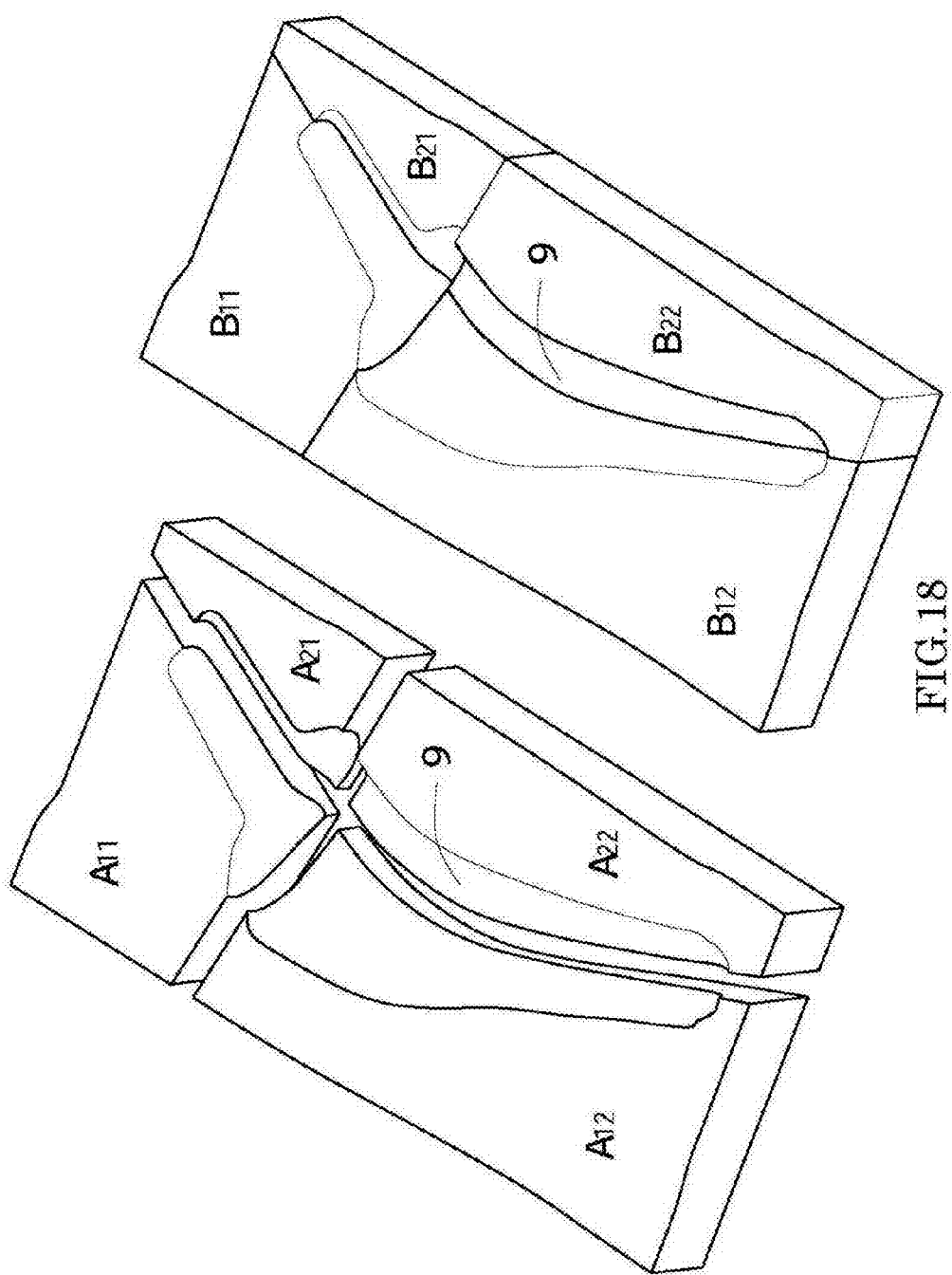
FIG. 18 is a schematic view of the mold consisting of eight blocks with their cavities being opened.

A and B with their cavities 9 being opened. FIG. 16 is a schematic view of the upper left, upper right, lower left and lower right blocks as molds $A_1$, $A_2$, $B_1$ and $B_2$ which are the left pieces and right pieces of molds A and B. These blocks may be stacked as shown in FIG. 17, showing the rear view of the upper mold B used for forming the upper outer shell and for final assembling of the stem, and the front view of the lower mold A used for forming the lower outer shell or the main structure lower half with the lower outer shell and for final assembling the stem. Each of the molds is divided into two parts to have right and left parts so as to facilitate the charge of the FRP structural elements, the close of mold and the removal of products from the mold. The hole 11*a* may often be on the boundary of the left and right blocks as illustrated in FIG. 16(*a*) and FIG. 17, because the position of the hole corresponds to the deepest spot in the cavity where the first sheet 7*a* is stacked. FIG. 18 shows an example of the mold consisting of eight blocks.

As it is clear from the above-mentioned, according to the structure of the hip-prosthesis stem, since the overlapping sections of the upper and lower outer shells are formed on the right and left portions of the integrated main structure, the shearing load is transmitted at these thick overlapping sections, meaning that the shearing load acting on the evenly stacked sheets can be reduced owing to the overlapping sections. These overlapping sections reinforce the evenly stacked FRP materials to give the stem much strength, durability and rigidity, and help the rest sections to promote the hoop effect in spite of the fact that they are thin films without overlapping sections. The inner structure having evenly stacked sheets is tightly hold by the overlapping sections, enabling the property of keeping the original shape of the stem to be close to that of a metallic stem.

Since the overlapping sections of the upper and lower outer shells are formed such that the left and right portions of the main structure formed by integrating the both halves have no stepped outer surface, undesirable unevenness is not formed on the surface of the stem. With a cement stem, it is advantageous to give an adhesive treatment uniformly on the surface of the stem. With a cement-less stem, it is advantageous to give a treatment of medicament for spongiosa bone growth, such as hydroxyapatite, effectively on the surface of the stem. Furthermore, it allows the stem to fit into the medullary cavity without inclination, which contributes to the improvement in Fit and Fill of the stem in the medullary cavity.

Since each of the main structure upper and lower halves has the structure such that the prepreg sheet having carbon fibers arranged at angle of 0/90 degrees and the prepreg sheet having carbon fibers arranged at angle of ±45 degrees are laminated alternately, semi-isotropy is promoted of each of the main structure upper and lower halves. The direction of the fibers at the cut end makes an angle of right, acute and obtuse relative to the tangential lines of the periphery of the sheet, which prevents the main structure from occurring cracks and separating resin from fibers. The fibers around the cut ends are closely intertwined with the fibers in the shells so as to promote the integration with the internal and external structures.

The outer shell is concavely curved to tightly cover the cavity of the mold, however the air void occurrence can be eliminated, because the outer shell is a thin prepreg sheet, as mentioned above. And the sheet is flexible to be made to fit the surface of the mold, the outer shell is precise in shape and size, thus the outer shell may be applicable to the above-mentioned cement-less stem which is required to be accurate both in shape and size. With the main structure, evenly stacking the sheets facilitates pressing out air bubbles therefrom, meaning that few air voids occur to raise the adhesiveness between layers, resulting in the improvement of durability of neck which receives the maximum load in the stem.

Whichever process mentioned above is applied to manufacturing the artificial hip prosthesis stem, it is necessary to wrap the mold containing the FRP structural elements in a bag made of heat resisting resin film. While heat and pressure are applied to the mold, the FRP structural elements stacked in the mold may tightly contact with each other by keeping a vacuum in the bag made of heat resisting resin film. Even if there is a slight slip caused by partial contact or extrusion of the elements before autoclaving, the mold is spontaneously closed during the curing operation.

Before evenly stacking the sheets for forming the main structure, a guide bar made of thermoplastic resin is disposed at the point where it certainly passes through the sheet to be initially stacked in each of the main structures, enabling the prepreg sheets not to slip while the sheets are stacked. The guide bar will melt during the curing operation to soak into the evenly stacked sheets, promoting the integration of the stacked sheets. Incidentally, as shown in FIG. 9, it is favorable to provide two or more guide bars 11, each of the bars may prevent the horizontally slipping of the sheets through which it passes.

The main structure lower half and the lower outer shell are previously integrated into one piece by applying heat before integrating the main structure upper half and the main structure lower half, enabling the process to be omitted of individually forming the main structure lower half, that is, it will not necessary to prepare the mold for forming only the main structure lower half whose cavity has to be lessened by a thickness of the outer shell. Decreasing the number of the mold required for forming the stem contributes to lowering of the manufacturing costs as a whole.

Figure 19:
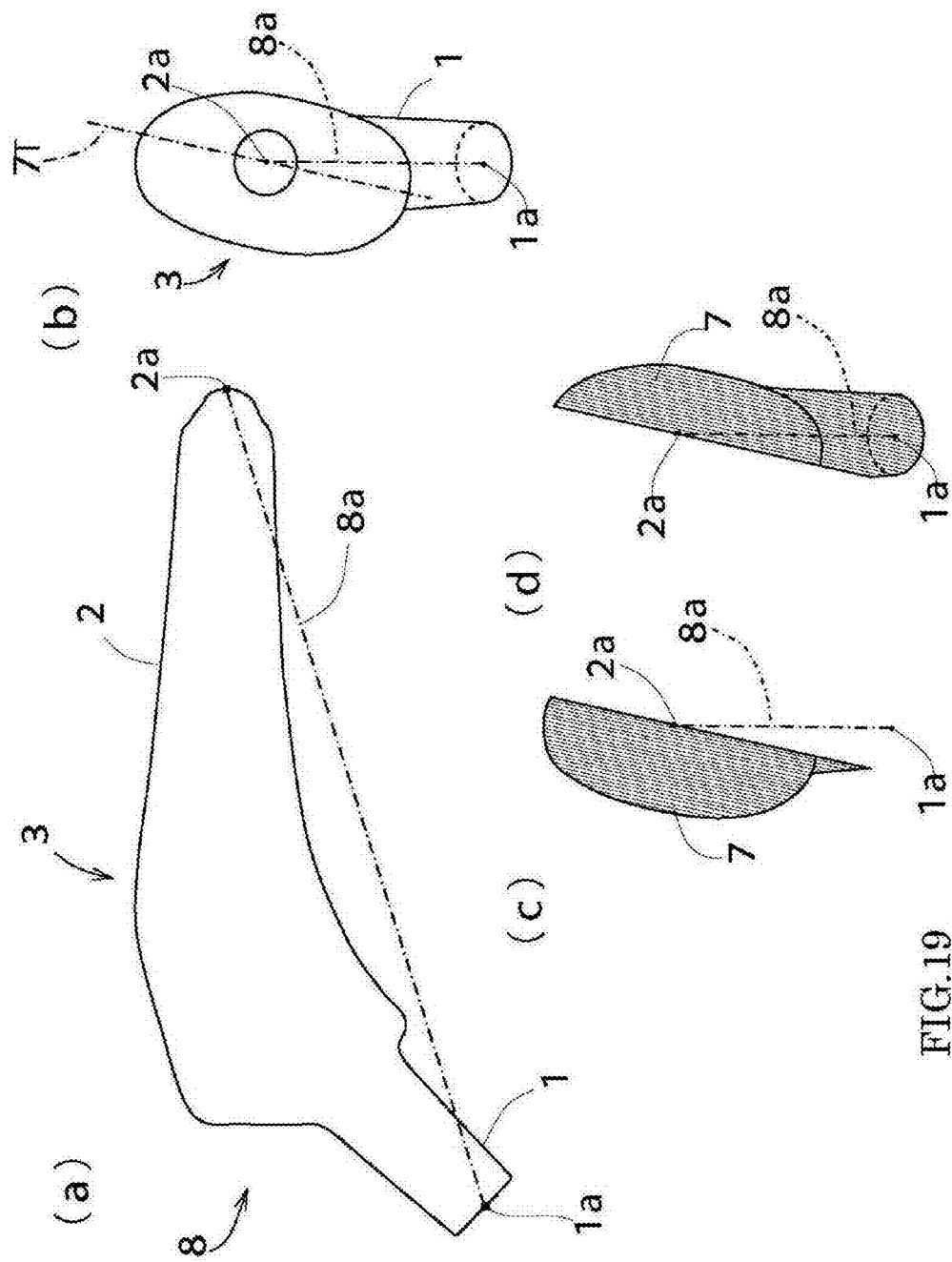
FIGS. 19(a)-19(d) are views for explaining another direction to extend the stacked prepreg sheets for the main structure upper and lower halves.

It has been explained so far that each of the flat surfaces of the prepreg sheets stacked for forming each of the main structure upper and lower halves is parallel to the plane containing the line 7S toward the direction giving the least loss of shearing load acting on the stem, alternately may be parallel to the plane being on a line toward the direction minimizing the number of the sheets to be stacked, as shown in FIG. 19(d). The flat surfaces of the stacked sheets parallel to the line 7T seem to be different from the line 7S giving the least loss of shearing load, but actually when within 18 degrees, since cosine 18 degrees is approximately equal to 0.95, the loss of shearing force can be limited to 5%. Minimizing the number of the sheets to be stacked enables the laborious working required for forming the main structure to be reduced.

Figure 20:
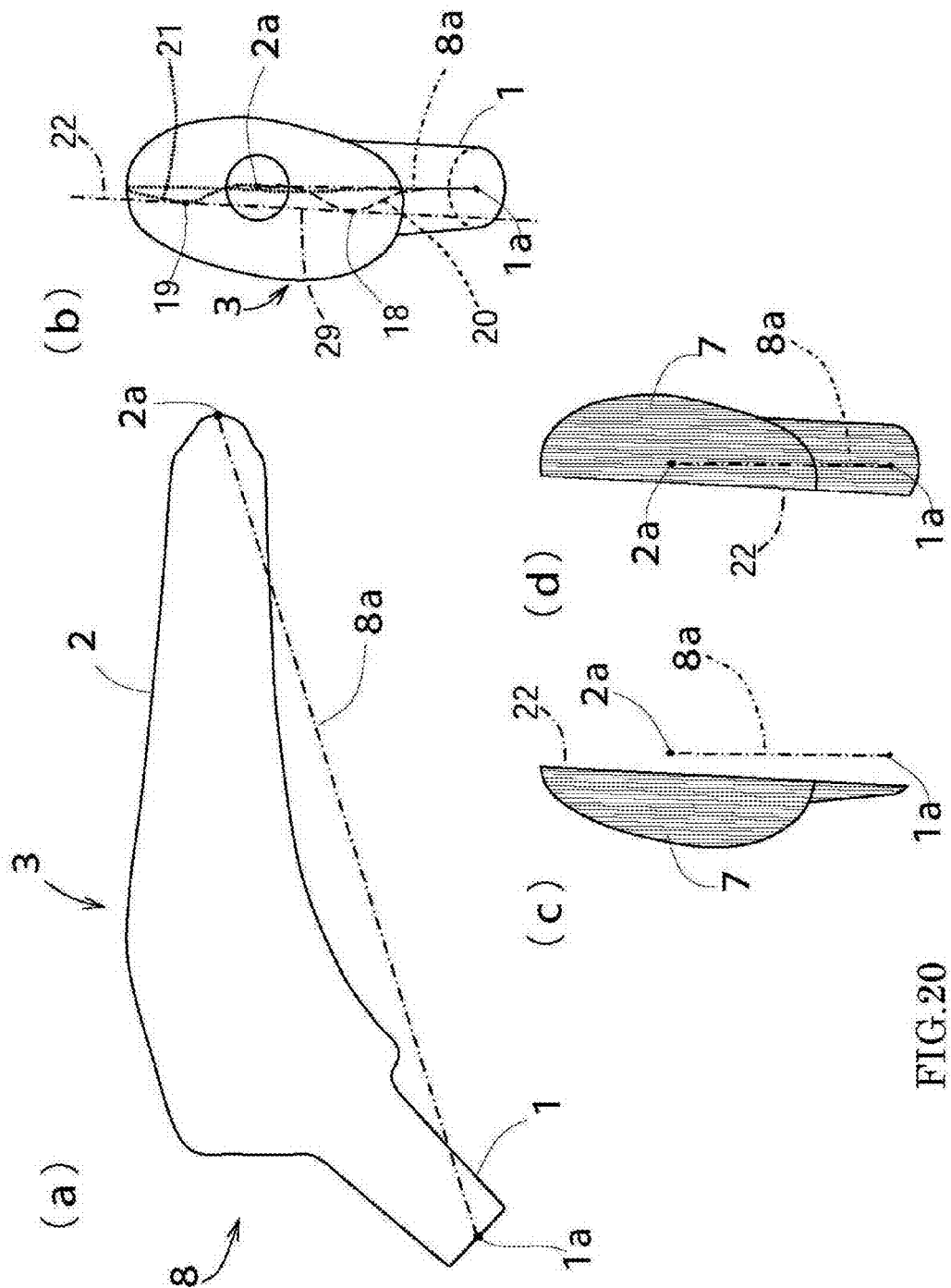
FIGS. 20(a)-20(d) are views for explaining furthermore another direction to extend the stacked prepreg sheets for the main structure upper and lower halves.

In selecting the directional line 7T, the line is best on the cross sectional plane which contains the highest points 18 and 19 of the largest part of the stem in width, shown in FIG. 20, and is parallel to the longitudinal reference line 8a as well. The cross sectional plane is selected to be a plane 22 for parting the mold, because it is advantageous for the top sheet 7n (see FIG. 7(e) and FIG. 12(c)) to cover the whole of the plane 22. The highest point 18 is the point which is on a line 20 connecting the edge points of the surfaces of every maximum width of the medial side of the stem placed in a flat state and the furthest from the longitudinal reference line 8a, the highest point 19 is the point which is on a line 21 connecting the edge points of the surfaces of every maximum width of the lateral side of the stem and is the furthest from the longitudinal reference line 8a. Thus at least one of the main structure upper and lower halves may have the shape such that the half can be easily removed from the mold (see FIG. 12 (g) for instance); that is, it will be sufficient to set the middle mold C to just one of the molds, for the upper half or the lower half, as shown in FIG. 7(e).

Figure 21:
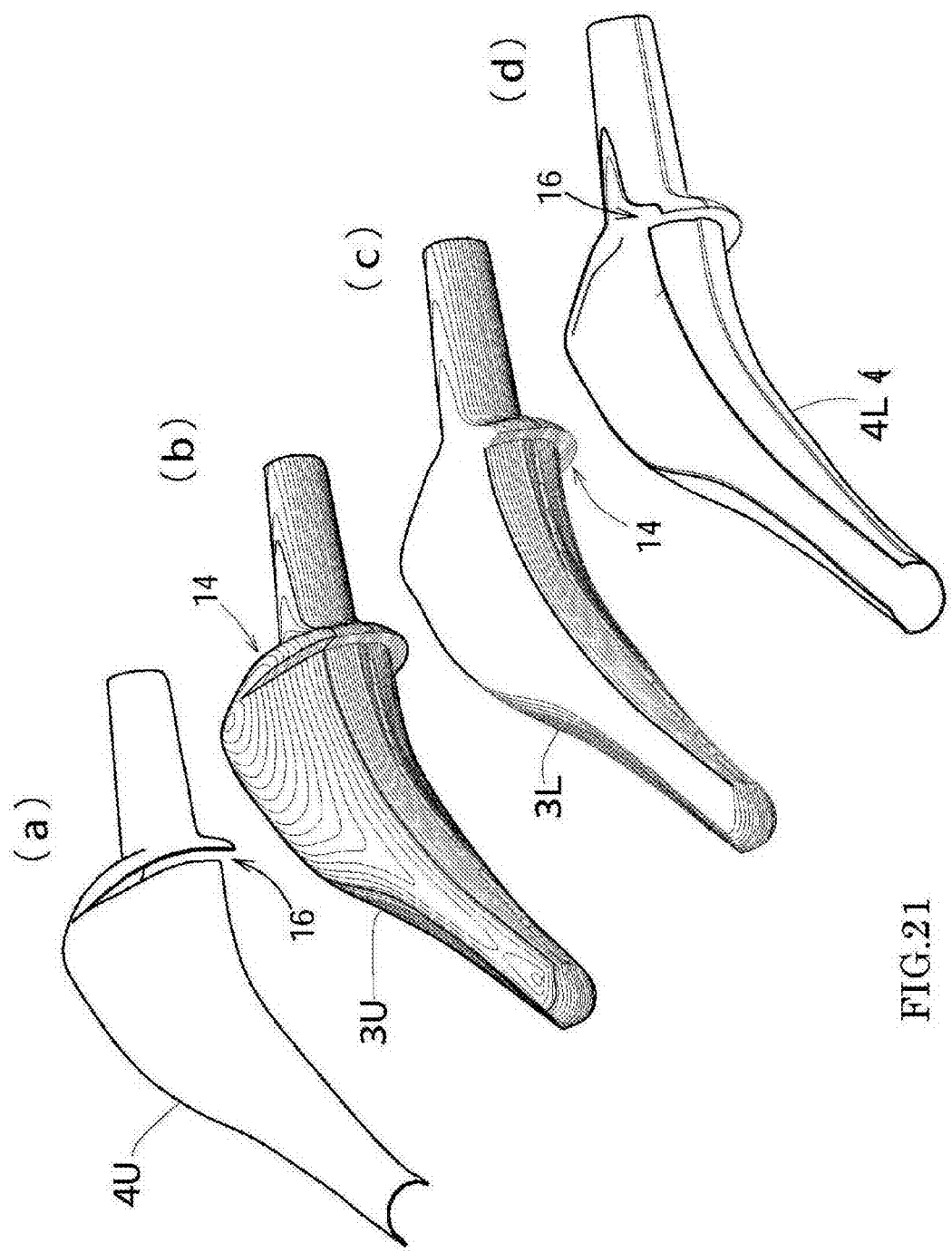
FIGS. 21(a)-21(d) are schematic views of each of the FRP structural elements for forming a stem provided with a fin sustaining itself in the hollow.
Figure 22:
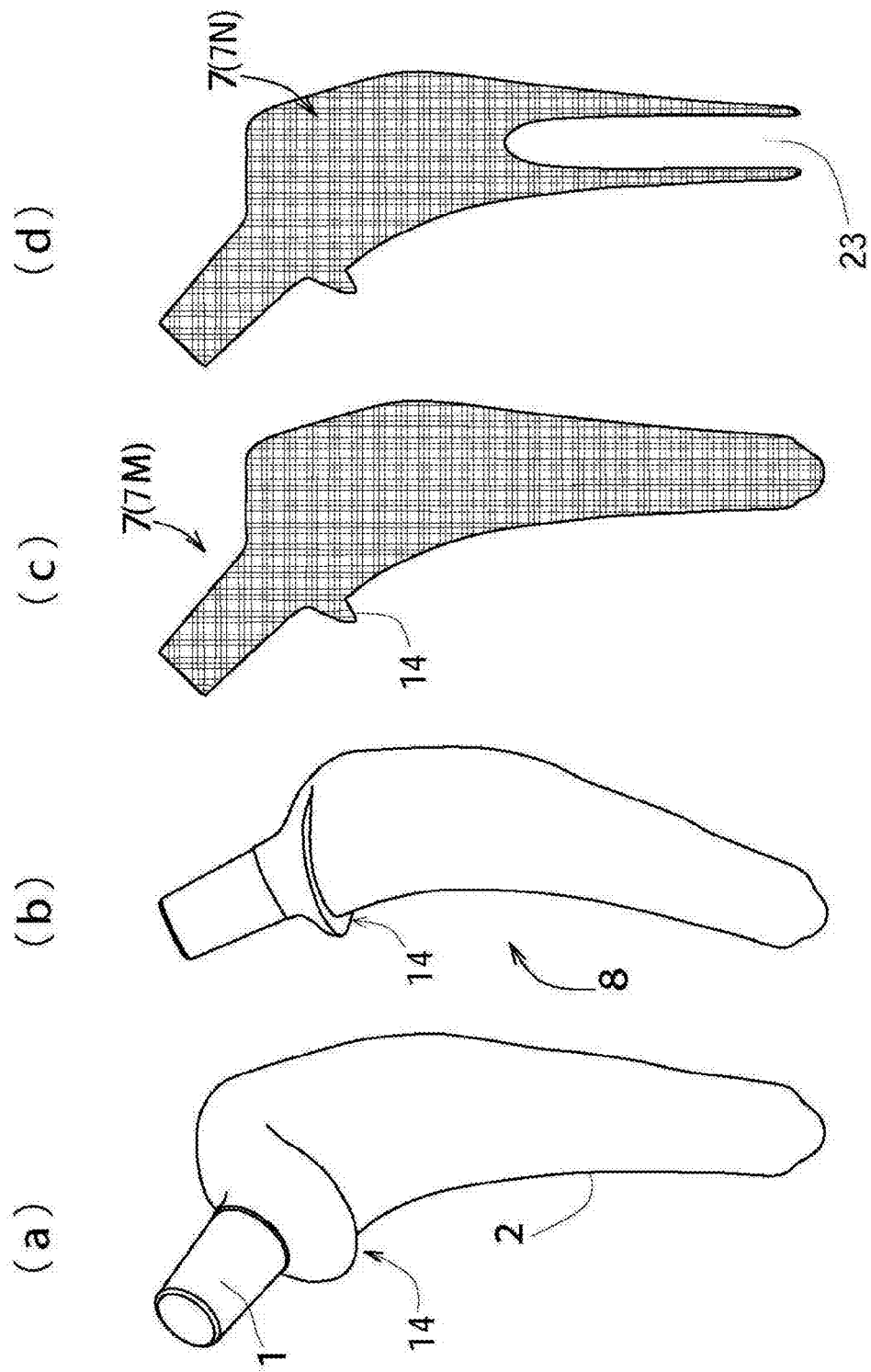
FIGS. 22(a)-22(d) are schematic views of a stem provided with a fin sustaining itself in the hollow and of the prepreg cutting sheets applicable thereto.
Figure 23:
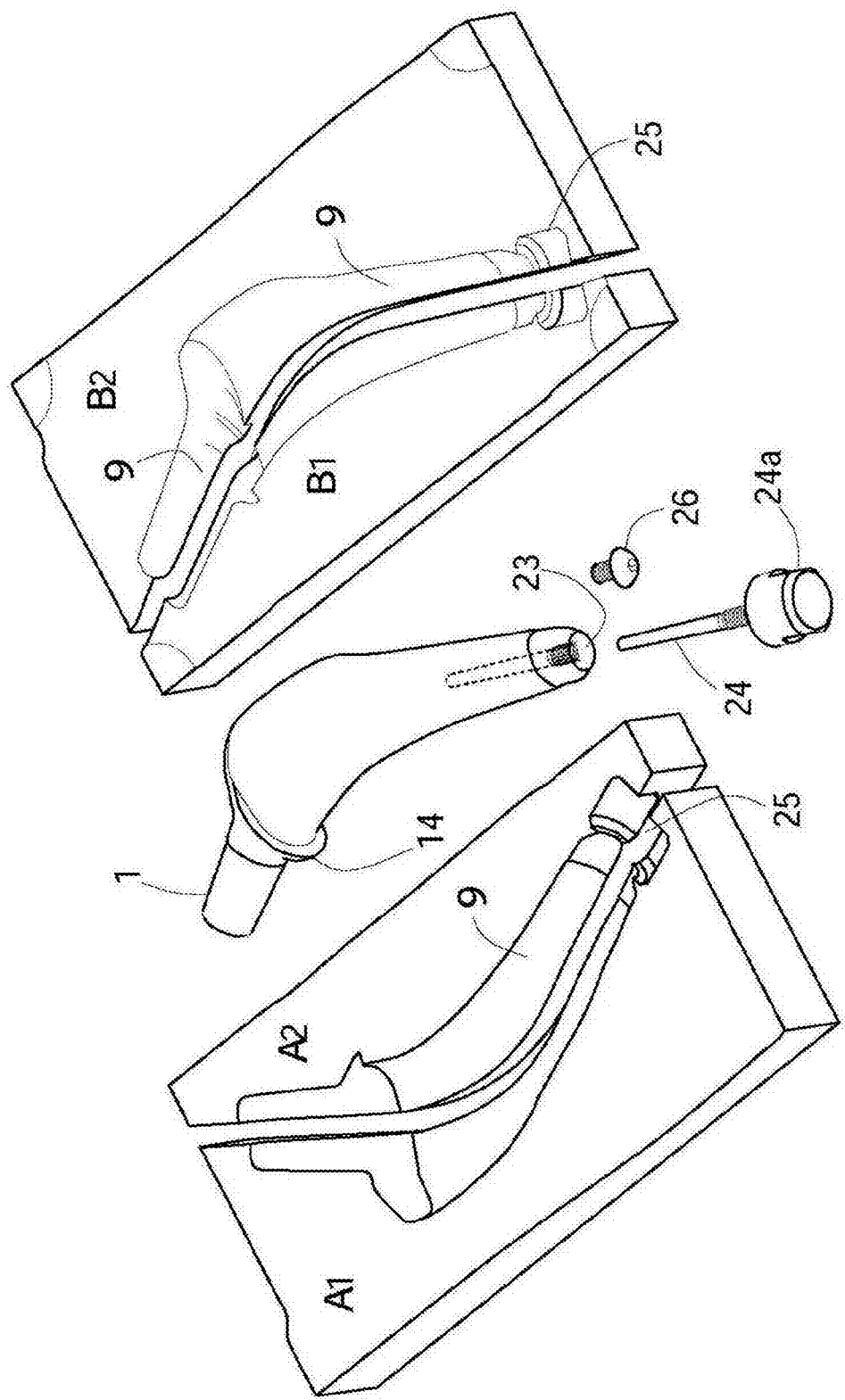
FIG. 23 is a schematic view of a stem provided with both a fin sustaining itself in the hollow and a deep hole opening toward diaphysis in the proximal portion thereof and a set of mold for forming the stem.
Figure 24:
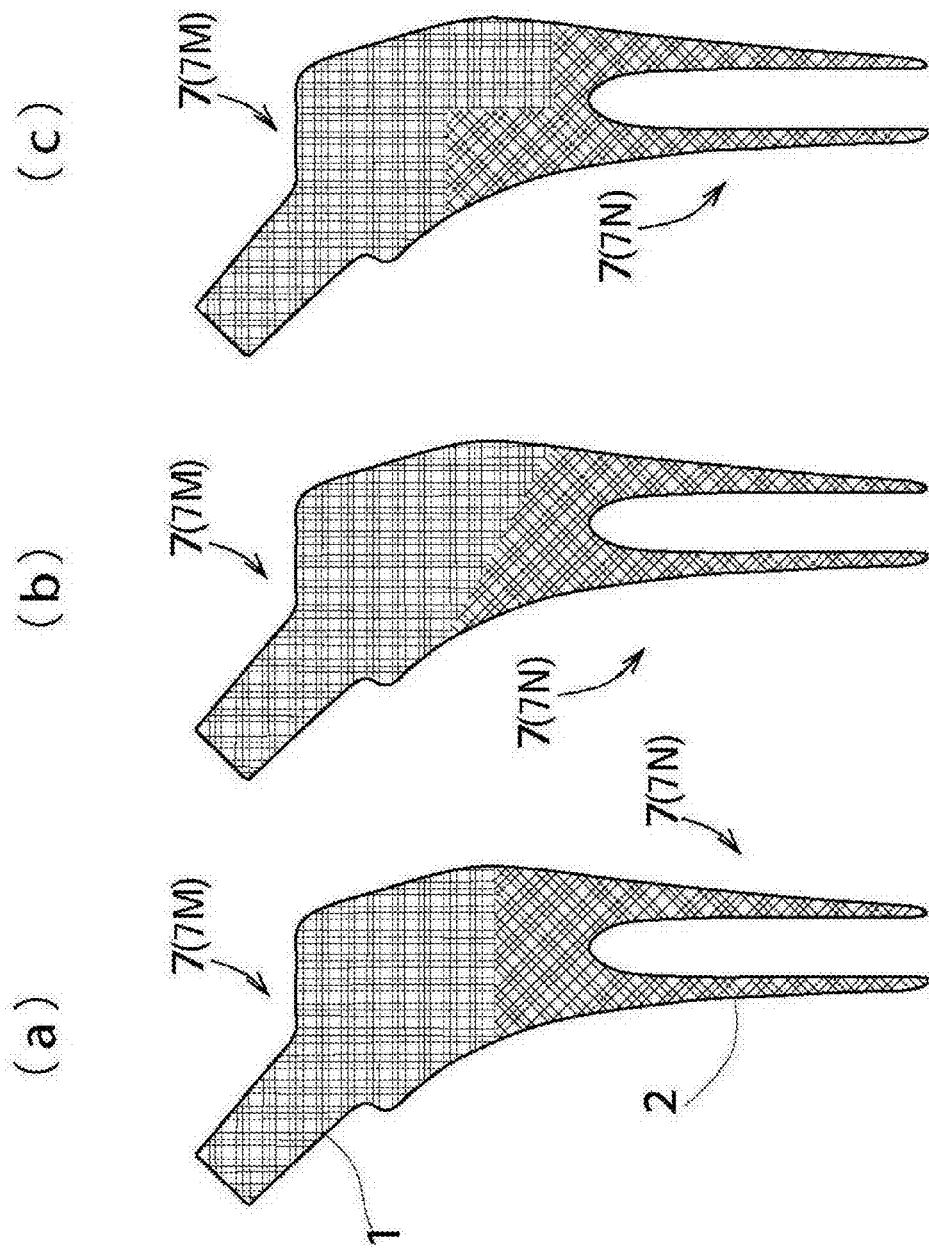
FIGS. 24(a)-24(c) are views of the surface of the prepreg cutting sheets evenly stacked for forming the main structure, showing other modifications of arrangement of the carbon fiber.
Figure 25:
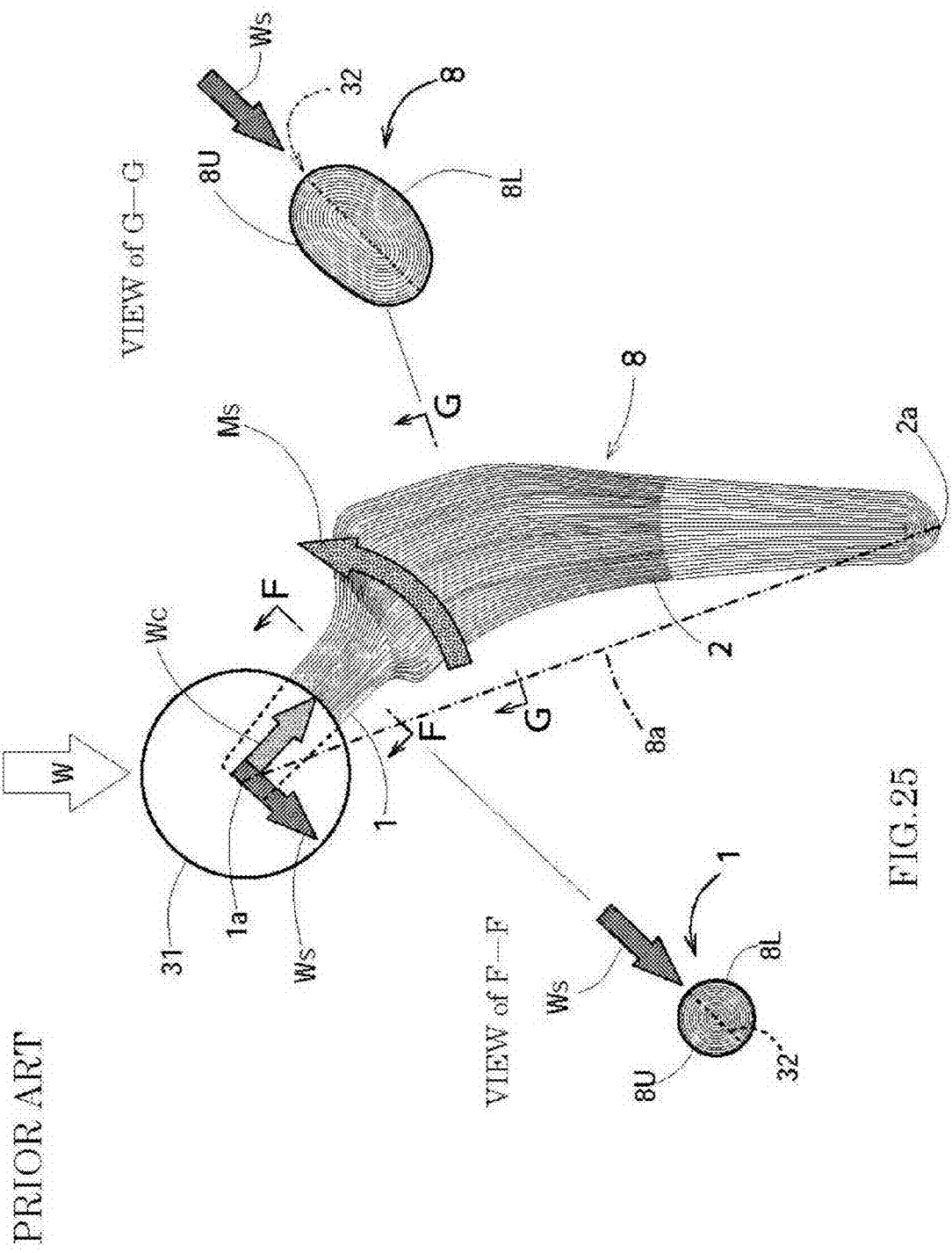
FIG. 25 is a view for showing a stem in which sheets are stacked by applying a conventional technology thereto and for explaining the load acting on the stem.
Figure 26:
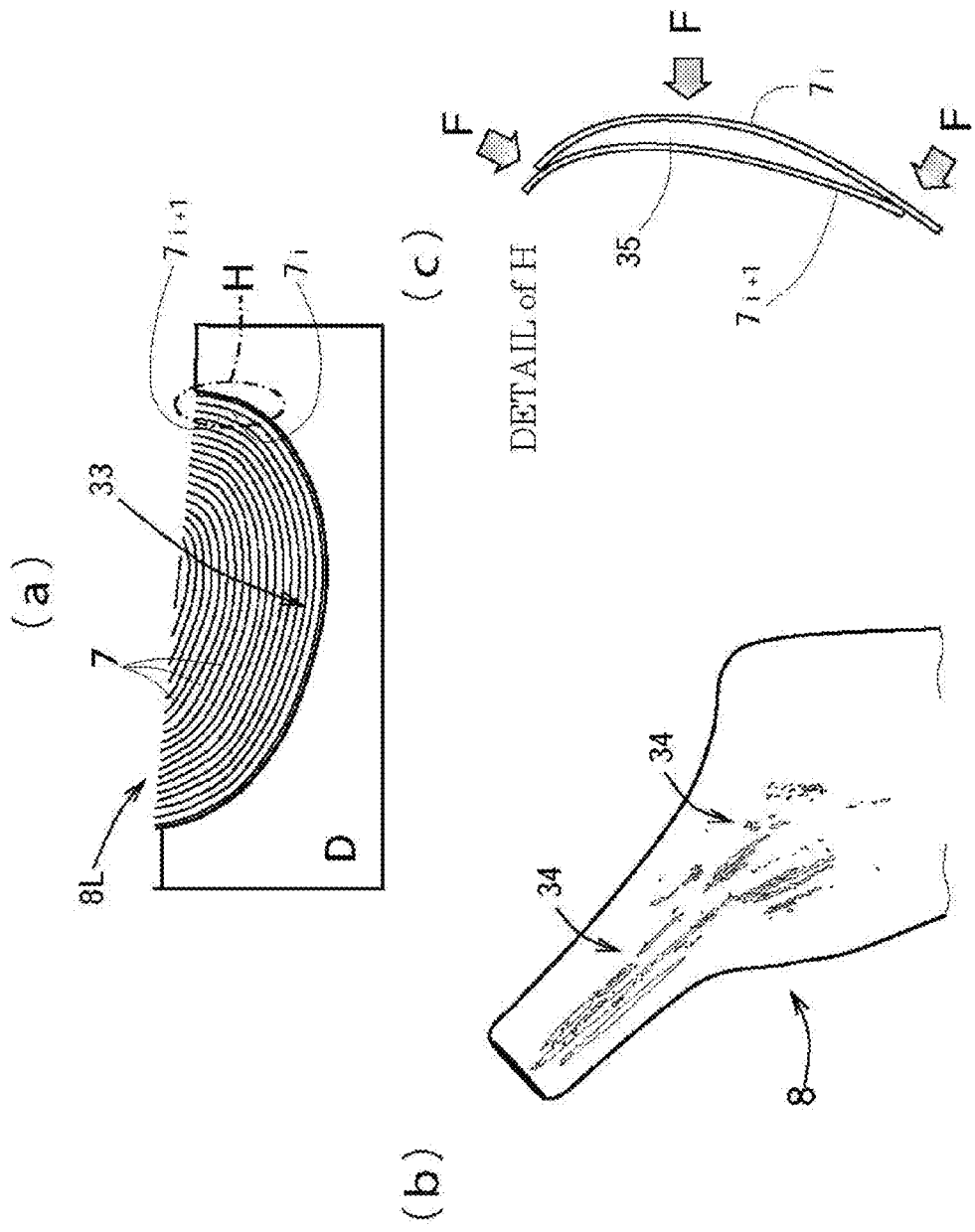
FIGS. 26(a)-26(c) are views for illustrating a cross section of a stem in which sheets are stacked by applying a conventional technology thereto and for explaining the occurrence of air voids in the stem.

FIG. 21 is an example of the FRP structural elements, where the upper end of the main structure 3 is provided with a fin 14 at the base of the neck 1. The fin is a part to hang on the edge of the opening of the medullary cavity in the medial side so that the stem 8 may not sink thereafter. The upper outer shell 4U and the lower outer shell 4L are provided with a slit 16 not so as to interfere with the fin which is made on the main structure upper half 3U and the main structure lower half 3L. FIG. 22(c) shows a prepreg cutting sheet 7 which is applicable to the largest cross section of the stem 8 such as (a) and (b). (d) shows a prepreg cutting sheet 7 to be used for reducing the stress-shielding by decreasing its rigidity owing to a hollow 23 made in the proximal portion of the stem. An example of a set of mold is shown in FIG. 23 where such prepreg cutting sheets are used. In the figure, 24 is a core for making a deep hole, 24a is a supporter of the core, 25 is a dent on the mold for holding the supporter of the core, 26 is a screw with a cap for shutting the deep hole 23 up. FIG. 24 shows three examples of the prepreg cutting sheets formed by combining the sheet 7M having carbon fibers arranged at angle of 0/90 degrees and the sheet 7N having carbon fibers arranged at angle of ±45 degrees.

The following is a list of symbols: 1: a neck, 1a: a center on the surface of upper end of the neck, 2: a body, 2a: a center in the end of diaphysis of the stem, 3: main structure, 3U: a main structure upper half, 3L: a main structure lower half, 3La: a main structure lower half integrated with a lower outer shell, 4: an outer shell, 4U: an upper outer shell, 4L: a lower outer shell, 5: overlapping sections, 6: a resin compound, 7: a prepreg cutting sheet, 7M: a sheet having carbon fibers arranged at angle of 0/90 degrees, 7N: a sheet having carbon fibers arranged at angle of ±45 degrees, 7S: a line toward the direction giving the least loss of shearing load, 7T: a line toward the direction minimizing the number of sheets, 8: a stem, 8a: a longitudinal reference line, 12: a bag made from heat resisting resin film, $W_s$: a component in the direction of shear, $M_s$: a moment caused by a load, A: a lower mold, B: an upper mold, C: a middle mold, B': an upper mold, A': a lower mold, C'.

The invention claimed is:

1. An artificial hip prosthesis stem formed by stacking fiberglass reinforced plastic materials, comprising:
    a stem having structural elements made from fiberglass reinforced plastic consisting of: an upper outer shell, a main structure upper half, a main structure lower half, and a lower outer shell when being divided in anterior and posterior directions into two halves to be placed in a flat state, and being integrated into one piece by stacking the fiberglass reinforced plastic structural elements and applying heat and pressure thereto to melt resins impregnated in each of the structural elements, and
    the upper outer shell and the lower outer shell being curved prepreg sheets formed by impregnating carbon fibers arranged at an angle substantially 45 degrees with a thermoplastic resin,
    the main structure upper and lower halves being evenly stacked parts in which prepreg sheets formed by impregnating carbon fiber with a thermoplastic resin are stacked, and
    overlapping sections of the upper and lower outer shells being formed such that the left and right portions of the main structure formed by integrating the both halves have no stepped outer surface.

2. The artificial hip prosthesis stem according to claim 1, wherein:
    said main structure upper and lower halves have pseudo-isotropy due to alternately stacking prepreg sheets having carbon fibers arranged at an angle of 0/90 degrees and prepreg sheets having carbon fibers arranged at an angle of substantially 45 degrees.

3. The artificial hip prosthesis stem according to claim 1, wherein:
    said upper and lower outer shells have films formed by melting resin compound on surfaces thereof.

4. The artificial hip prosthesis stem according to claim 1, wherein:
    flat surfaces of each of the prepreg sheets evenly stacked in said main structure upper and lower halves is parallel to a plane both containing a longitudinal reference line linking a center on the surface of an upper end of a neck for supporting the spherical joint and a center in an end of a diaphysis of the stem, and being on a line toward a direction giving a least loss of shearing load acting on the stem.

5. The artificial hip prosthesis stem according to claim 1, wherein:

flat surfaces of each of the prepreg sheets evenly stacked in said main structure upper and lower halves is parallel to a plane both containing said longitudinal reference line and being on a line toward a direction minimizing a number of sheets to be stacked.

6. A method for manufacturing an artificial hip prosthesis stem according to claim 1, comprising:

entirely wrapping a mold containing said fiberglass reinforced plastic structural elements in a bag made of a heat resisting resin film, keeping a vacuum in said bag made of heat resisting resin film while heat and pressure are applied to the mold.

* * * * *